(12) United States Patent
Gibson et al.

(10) Patent No.: US 7,012,083 B2
(45) Date of Patent: Mar. 14, 2006

(54) COMPOUNDS USEFUL IN THERAPY

(75) Inventors: Stephen Paul Gibson, Sandwich (GB);
Ivan Tommasini, Sandwich (GB);
David Morris Gethin, Sandwich (GB);
Richard Edward Armer, Newhouse (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/108,161

(22) Filed: Mar. 27, 2002

(65) Prior Publication Data
US 2002/0099214 A1  Jul. 25, 2002

Related U.S. Application Data

(63) Continuation of application No. 09/571,257, filed on May 15, 2000, now abandoned.

(30) Foreign Application Priority Data
May 28, 1999 (GB) .................... 9912416

(51) Int. Cl.
*C07D 211/06* (2006.01)
*A61K 31/445* (2006.01)
(52) U.S. Cl. .................... 514/317; 546/192
(58) Field of Classification Search ........ 546/192; 514/317
See application file for complete search history.

(56) References Cited

U.S. PATENT DOCUMENTS

| | | | |
|---|---|---|---|
| 4,081,450 A | 3/1978 | Zimmerman | |
| 4,191,771 A | 3/1980 | Zimmerman | |
| 4,284,635 A | * 8/1981 | Zimmerman | ............. 514/317 |
| 5,136,040 A | 8/1992 | Werner | |
| 5,498,718 A | 3/1996 | Werner | |
| 5,610,271 A | 3/1997 | Dooley et al. | |

FOREIGN PATENT DOCUMENTS

| | | |
|---|---|---|
| DE | 4341403 | 6/1995 |
| EP | 0013078 | 7/1980 |
| EP | 0136863 | 4/1985 |
| EP | 0506468 A1 | 9/1992 |
| EP | 0506478 A1 | 9/1992 |
| EP | 0287339 | 8/1994 |
| EP | 0506468 B1 | 4/1995 |
| EP | 0657428 | 6/1995 |
| EP | 0755923 | 1/1997 |
| EP | 0506478 B1 | 9/1997 |
| EP | 0938898 | 9/1999 |
| GB | 1525584 | 9/1978 |
| GB | 2038812 | 11/1979 |
| WO | 95/15327 | 6/1995 |
| WO | WO 99/23072 | 5/1999 |
| WO | 99/59971 | 11/1999 |
| WO | 00/39089 | 7/2000 |

OTHER PUBLICATIONS

Zimmerman, "Structure-Activity Relationship of Trans-3,4-Dimethyl-4-(3-hydroxypheyl) Antagonists for $\mu$- and $_k$-Opioid Receptors", *J. Med. Chem.* 283-2850 (1993).

Mitch, et al., "3,4-Dimethyl-4-(3-hydroxyphenyl) Piperidines: Opioid Antagonists with Potent Anorectant Activity", *J. Med. Chem.* 283-2850 (1993).

Thomas, et al., "Investigation of the N-Substituent Conformation Governing Potency and $\mu$ Receptor Subtype-Selectivity in (+)-(3R,3R)-Dimethyl-4-(3-hydroxyphenyl)-Piperidine Opioid Antagonists", *J. Med. Chem.* 41:980-1990 (1998).

Gisela R. Heyer, et al., "Recent Studies of Cutaneous Nociception in Atopic and Non-Atopic Subjects", The Journal of Dermatology, 26(2):77-86 (1999).

Chun-Su Yuan, et al., "Efficacy of Orally Administered Methyinaltrexone in Decreasing Subjective Effects After Intravenous Morphine", Drug and Alcohol Dependence, 52:161-165 (1998).

Nora Valeria Bergasa, et al., "Effects of Naloxone Infusions in Patients with the Pruritus of Cholestasis", American College of Physicians, 123:161-167 (1995).

Sophia Georgala, et al., "Raised $\beta$-endorphin Serum Levels in Children with Atopic Dermatitis and Pruritus", Journal of Dermatrological Science, 8:125-128 (1994).

Dennis M. Zimmerman, et al., "Structure-Activity Relationships of trans-3,4-Dimethyl-4-(3-hydroxyphenyl) piperidine Antagonists for u- and k-Opioid Receptors", Journal of Medicinal Chemistry, 36(20):2833-2841 (1993).

* cited by examiner

*Primary Examiner*—Zinna Northington Davis
(74) *Attorney, Agent, or Firm*—Gregg C. Benson; Arlene K. Musser

(57) ABSTRACT

There is provided a compound of formula I,

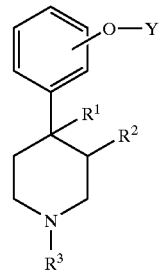

wherein $R^1$, $R^2$, $R^3$ and Y have meanings given in the description, which are useful in the prophylaxis and in the treatment of pruritus.

13 Claims, No Drawings

COMPOUNDS USEFUL IN THERAPY

RELATED APPLICATION

The present application is a continuation of U.S. Ser. No. 09/571,257 filed on May 15, 2000 now abandoned, which claims priority of Great Britain Application No. GB 9912416.6 filed on May 28, 1999.

This invention relates to novel 4-phenylpiperidines having utility in the treatment of pruritic dermatoses including allergic dermatitis and atopy in animals and humans, and processes for the preparation of and intermediates used in the preparation of such compounds.

BACKGROUND OF THE INVENTION

Field of the Invention

Itching or pruritus is a common dermatological symptom which can give rise to considerable distress, in both humans and animals. Pruritus is often associated with inflammatory skin disease which can commonly be caused by hypersensitivity reactions, such as reaction to insect bites e.g. flea bites, or to environmental allergens such as house dust mite or pollen; or by bacterial and fungal infections of the skin or ectoparasite infections. Previous treatments for pruritus include the use of corticosteroids and antihistamines, however both have undesired side effects. Other therapies include the use of essential fatty acid dietary supplements which are slow to act and offer only limited efficacy against allergic dermatitis. A variety of emollients such as soft paraffin, glycerine and lanolin are also employed but with limited success and there is a continuing need for an effective remedy.

Certain 1,3,4-trisubstituted 4-aryl-piperidine derivatives are disclosed in GB-A-1525584 as potent narcotic antagonists which also display analgesic properties. These compounds are also claimed in EP-B-0287339 as opioid antagonists which block the effect of agonists at the mu or kappa receptors having potential utility in treating a variety of disorders associated with these receptors such as eating disorders, opiate overdose, depression, smoking, alcoholism, sexual dysfunction, shock, stroke, spinal damage and head trauma; utility as an appetite suppressant for weight loss has also been suggested. Further related 1-N-substituted-4-aryl piperidines are disclosed in EP-A-0506468 and EP-A-0506478. Potential utility is suggested in preventing peripherally mediated undesired opiate effects and in relieving the symptoms of idiopathic constipation and irritable bowel syndrome.

According to the present invention we provide novel 4-phenylpiperidines which are, and/or are prodrugs of, potent and effective antipruritic agents.

SUMMARY OF THE INVENTION

Thus, the present invention provides compounds of formula I:

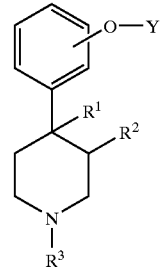

wherein
$R^1$ and $R^2$ are each independently H or $C_{1-4}$ alkyl;
$R^3$ represents aryl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$), $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{4c}$, $S(O)_n R^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2 R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $-W-A^1-N(R^{5b})(R^{5c})$;
n is 0, 1 or 2;
W represents a single bond, C(O) or $S(O)_p$;
$A^1$ represents a single bond or $C_{1-10}$ alkylene;
provided that when both W and $A^1$ represent single bonds, then the group $-N(R^{5b})(R^{5c})$ is not directly attached to an unsaturated carbon atom;
p is 0, 1 or 2;
$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;
provided that $R^{4d}$ does not represent H when n represents 1 or 2;
$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $Het^3$, or $R^{5b}$ and $R^{5c}$ together represent unbranched $C_{2-6}$ alkylene which alkylene group is optionally interrupted by O, S and/or an $N(R^7)$ group and is optionally substituted by one or more $C_{1-4}$ alkyl groups;
$R^6$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;

R$^7$ represents H, C$_{1-6}$ alkyl, C$_{3-8}$ cycloalkyl, A$^2$-(C$_{3-8}$ cycloalkyl) or A$^2$-aryl;

A$^2$ represents C$_{1-6}$ alkylene;

Het$^1$, Het$^2$ and Het$^3$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, C$_{1-4}$ alkyl, C$_{1-4}$ alkoxy and C$_{1-5}$ alkanoyl (which latter three groups are optionally substituted by one or more halo atoms);

Y represents —C(=E)NR$^8$R$^9$, C(O)R$^{10}$, C(O)OR$^{10a}$, C(O)CH(R$^{10b}$)N(G)G$^a$, R$^{11}$, CH(R$^{12b}$)C(O)OR$^{12a}$, CH(R$^{12b}$)OCO$_2$R$^{12a}$, C(O)C(R$^{13a}$)=C(R$^{13b}$)NH$_2$, C(O)CH(R$^{13a}$)CH(NH$_2$)(R$^{13b}$) or PO(OR$^{14}$)$_2$;

E represents O or S;

R$^8$ and R$^9$ independently represents H, C$_{1-10}$ alkyl, C$_{3-10}$ alkenyl (which latter two groups are optionally substituted by one or more aryl or C$_{4-7}$ cycloalkyl groups (which two groups are optionally substituted by one or more substituents selected from halo, C$_{1-4}$ alkyl, C$_{1-4}$ alkoxy, C$_{1-4}$ haloalkyl or C$_{1-4}$ haloalkoxy)), aryl, C$_{4-7}$ cycloalkyl (optionally substituted by one or more substituents selected from halo, C$_{1-4}$ alkyl and C$_{1-4}$ alkoxy (which latter two groups are optionally substituted by one or more halo atoms)), or R$^8$ and R$^9$, together with the N-atom to which both are attached, represent Het$^4$;

Het$^4$ represents a 5- to 8-membered heterocyclic ring comprising at least one nitrogen atom and optionally one or more additional heteroatoms selected from oxygen and sulfur, which heterocyclic ring is optionally substituted by one or more C$_{1-4}$ alkyl groups;

R$^{10}$ represents H, C$_{4-7}$ cycloalkyl (optionally substituted by one or more C$_{1-4}$ alkyl groups), C$_{1-11}$ alkyl (substituted by one or more substituents selected from aryl (optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl, C$_{1-4}$ alkoxy, C$_{1-4}$ haloalkyl and C$_{1-4}$ haloalkoxy) or C$_{4-7}$ cycloalkyl (which latter group is optionally substituted by one or more C$_{1-4}$ alkyl groups)) or aryl (optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl and C$_{1-4}$ alkoxy (which latter two groups are optionally substituted by one or more halo atoms));

R$^{10a}$ represents C$_{4-7}$ cycloalkyl (optionally substituted by one or more C$_{1-4}$ alkyl groups), C$_{1-11}$ alkyl (optionally substituted by one or more substituents selected from aryl (optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl, C$_{1-4}$ alkoxy, C$_{1-4}$ haloalkyl and C$_{1-4}$ haloalkoxy) or C$_{4-7}$ cycloalkyl (which latter group is optionally substituted by one or more C$_{1-4}$ alkyl groups)), aryl (optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl and C$_{1-4}$ alkoxy (which latter two groups are optionally substituted by one or more halo atoms)) or Het$^5$;

R$^{10b}$ represents H, C$_{4-7}$ cycloalkyl, C$_{1-10}$ alkyl (optionally substituted by one or more substituents selected from aryl or C$_{4-7}$ cycloalkyl), aryl, or R$^{10b}$ (optionally in conjunction with G$^a$) represents a naturally occurring amino acid substituent;

G and G$^a$ independently represent H, an amino protective group, or G$^a$, together with R$^{10b}$, represents a naturally occurring amino acid substituent;

R$^{11}$ represents C$_{4-7}$ cycloalkyl (optionally substituted by one or more C$_{1-4}$ alkyl groups), aryl (optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl and C$_{1-4}$ alkoxy (which latter two groups are optionally substituted by one or more halo atoms)), C$_{6-10}$ alkyl, C$_{3-10}$ alkenyl, which alkyl or alkenyl group is optionally substituted by one or more substituents selected from C(O)NH$_2$, Het$^6$, C$_{4-7}$ cycloalkyl (optionally substituted by one or more C$_{1-4}$ alkyl groups), aryl, aryloxy or aryl(C$_{1-4}$)alkoxy (which latter three groups are optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl and C$_{1-4}$ alkoxy (which latter two groups are optionally substituted by one or more halo atoms)), or R$^{11}$ represents Het$^7$ or C$_{1-5}$ alkyl substituted by one or more substituents selected from C(O)NH$_2$, Het$^8$, C$_{4-7}$ cycloalkyl (optionally substituted by one or more C$_{1-4}$ alkyl groups), aryl, aryloxy or aryl(C$_{1-4}$)alkoxy (which latter three groups are optionally substituted by one or more substituents selected from OH, halo, C$_{1-4}$ alkanoyl, C$_{1-4}$ alkanoyloxy, N(R$^8$)(R$^9$), C(O)N(R$^8$)(R$^9$), C$_{1-4}$ alkyl and C$_{1-4}$ alkoxy (which latter two groups are optionally substituted by one or more halo atoms));

Het$^5$ to Het$^8$ independently represent 4- to 6-membered heterocyclic rings, which rings contain at least one heteroatom selected from oxygen, sulfur, and/or nitrogen, which rings are optionally fused to a benzene ring, and which rings are optionally substituted in the heterocyclic and/or fused benzene ring part by one or more substituents selected from OH, =O, nitro, amino, halo, CN, aryl, C$_{1-4}$ alkyl, C$_{1-4}$ alkoxy, C$_{3-6}$ cycloalkyl and C$_{1-5}$ alkanoyl (which latter four groups are optionally substituted by one or more halo atoms);

R$^{12a}$ and R$^{12b}$ independently represent H, C$_{4-7}$ cycloalkyl (optionally substituted by one or more C$_{1-4}$ alkyl groups), C$_{1-10}$ alkyl (optionally substituted by one or more substituents selected from aryl or C$_{4-7}$ cycloalkyl (which latter group is optionally substituted by one or more C$_{1-4}$ alkyl groups)) or aryl (optionally substituted by one or more is substituents selected from OH, halo, C$_{1-4}$ alkanoyl, C$_{1-4}$ alkanoyloxy, C$_{1-4}$ alkyl and C$_{1-4}$ alkoxy (which latter two groups are optionally substituted by one or more halo atoms));

R$^{13a}$ and R$^{13b}$ independently represent H, C$_{4-7}$ cycloalkyl (optionally substituted by one or more C$_{1-4}$ alkyl groups), C$_{1-10}$ alkyl, C$_{2-10}$ alkenyl (which alkyl and alkenyl groups are optionally substituted by one or more substituents selected from aryl or C$_{4-7}$ cycloalkyl (which latter group is optionally substituted by one or more C$_{1-4}$ alkyl groups)), or aryl (optionally substituted by one or more substituents selected from OH, halo, C$_{1-4}$ alkanoyl, C$_{1-4}$ alkanoyloxy, C$_{1-4}$ alkyl and C$_{1-4}$ alkoxy (which latter two groups are optionally substituted by one or more halo atoms));

R$^{14}$ represents H, C$_{4-7}$ cycloalkyl (optionally substituted by one or more C$_{1-4}$ alkyl groups), C$_{1-10}$ alkyl (optionally substituted by one or more substituents selected from aryl or C$_{4-7}$ cycloalkyl (which latter group is optionally substituted by one or more C$_{1-4}$ alkyl groups)), or aryl (optionally substituted by one or more substituents selected from OH, halo, C$_{1-4}$ alkanoyl, C$_{1-4}$ alkanoyloxy, C$_{1-4}$ alkyl and C$_{1-4}$ alkoxy (which latter two groups are optionally substituted by one or more halo atoms));

or pharmaceutically, or veterinarily, acceptable derivatives thereof; which compounds are referred to together hereinafter as "the compounds of the invention."

DETAILED DESCRIPTION OF THE INVENTION

In the definitions used herein, alkyl, alkylene, alkoxy, alkoxy carbonyl, alkanoyl, alkanoyloxy, alkenyl, alkynyl and the alkyl parts of alkylphenyl and aryl alkoxy groups may, when there is a sufficient number of carbon atoms, be straight or branched-chain and/or optionally interrupted by one or more oxygen and/or sulfur atom(s). The term halo includes fluoro, chloro, bromo or iodo. The term "aryl" includes optionally substituted phenyl, naphthyl and the like, and "aryloxy" includes optionally substituted phenoxy and naphthyloxy and the like. Unless otherwise specified, aryl and aryloxy groups are optionally substituted by one or more (e.g. one to three) substituents selected from OH, nitro, amino, halo, CN, $CH_2CN$, $CONH_2$, $C_{1-4}$ alkyl, $C_{1-4}$ alkoxy $C_{1-4}$ alkoxy carbonyl and $C_{1-5}$ alkanoyl (which latter four groups are optionally substituted by one or more halo atoms).

The heterocyclic rings that $Het^1$, $Het^2$, $Het^3$, $Het^4$, $Het^5$, $Het^6$, $Het^7$ and $Het^8$ represent may be fully saturated, partially unsaturated and/or wholly or partially aromatic in character. Specific rings that may be mentioned include: for $Het^1$, dioxane, dioxolane, morpholine, piperidine, perhydroazepine, pyrazole, pyridine, triazole, tetrahydrofuran, tetrahydropyran, pyrrole, pyrrollidine or tetrazole; for $Het^2$, tetrahydropyran.

For the avoidance of doubt, when Het ($Het^1$, $Het^2$, $Het^3$, $Het^4$, $Het^5$, $Het^6$, $Het^7$ and $Het^8$) groups are at least part-saturated, possible points of substitution include the atom (e.g. the carbon atom) at the point of attachment of the Het group to the rest of the molecule. Het groups may also be attached to the rest of the molecule via a heteroatom.

The piperidine moiety in compounds of formula I may be in N-oxidised form. Sulfur atoms that may interrupt (e.g. alkyl) substituents in compounds of formula I may be present in oxidised form (e.g. as sulfoxides or sulfones). All $Het^1$, $Het^2$, $Het^3$, $Het^4$, $Het^5$, $Het^6$, $Het^7$ and $Het^8$ groups may also be in N- or S-oxidized forms.

The term "amino protective group" as used herein will be understood by the skilled person to include those mentioned in "Protective Groups in Organic Synthesis", $2^{nd}$ edition, T W Greene & P G M Wutz, Wiley-Interscience (1991), in particular those indexed at pages 218 to 222 of that reference, the disclosure in which document is hereby incorporated by reference.

Specific examples of amino protective groups thus include carbamate groups (e.g. methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-trimethylsilylethyl, 2-methylthioethyl, 2-methylsulfonylethyl, 2(p-toluenesulfonyl)ethyl, 2-phosphonioethyl, 1,1-dimethylpropynyl, 1,1-dimethyl-3-(N,N-dimethylcarboxamido)propyl, 1,1-dimethyl-3-(N,N-diethylamino)propyl, 1-methyl-1-(1-adamantyl)ethyl, 1-methyl-1-phenylethyl, 1-methyl-1-(3,5-dimethoxyphenyl)ethyl, 1-methyl-1-(4-biphenylyl)ethyl, 1-methyl-1-(p-phenylazophenyl)ethyl, 1,1-dimethyl-2-haloethyl, 1,1-dimethyl-2,2,2-trichloroethyl, 1,1-dimethyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4,6-tri-t-butylphenyl, m-nitrophenyl, S-phenyl, 8-quinolinyl, N-hydroxypiperidinyl, 4-(1,4-dimethylpiperidinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitrobenzyl, o-nitrobenzyl, 3,4-dimethoxy-6-nitrobenzyl, p-bromobenzyl, chlorobenzyl, 2,4-dichlorobenzyl, p-cyanobenzyl, o-(N,N-dimethylcarboxamidobenzyl)benzyl, m-chloro-p-acyloxybenzyl, p-(dihydroxyboryl)benzyl, p-(phenylazo)benzyl, p-(p-methoxyphenylazo)benzyl, 5-benzisoxazolyl-methyl, 9-anthrylmethyl, diphenylmethyl, phenyl(o-nitrophenyl)methyl, di(2-pyridyl)methyl, 1-methyl-1-(4-pyridyl)ethyl, isonicotinyl or S-benzyl carbamate groups), amide groups (e.g. N-formyl, N-acetyl, N-chloroacetyl, N-dichloroacetyl, N-trichloroacetyl, N-trifluoroacetyl, N-o-nitrophenylacetyl, N-o-nitrophenoxyacetyl, N-acetoacetyl, N-acetylpyridinium, N-3-phenylpropionyl, N-3-(p-hydroxybenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-isobutyryl, N-o-nitrociniamoyl, N-picolinoyl, N-(N'-acetylmethionyl), N-(N'-benzoylphenylalanyl), N-benzoyl, N-p-phenylbenzoyl, N-p-methoxybenzoyl, N-o-nitrobenzoyl or N-o-(benzoyloxymethyl)benzoyl amide groups), alkyl groups (e.g. N-allyl, N-phenacyl, N-3-acetoxypropyl, N-(4-nitro-1-cyclohexyl-2-oxo-pyrrolin-3-yl), N-methoxymethyl, N-chloroethoxymethyl, N-benzyloxymethyl, N-pivaloyloxymethyl, N-2-tetrahydropyranyl, N-2,4-dinitrophenyl, N-benzyl, N-3,4-dimethoxybenzyl, N-o-nitrobenzyl, N-di(p-methoxyphenyl)methyl, N-triphenylmethyl, N-(p-methoxyphenyl)diphenylmethyl, N-diphenyl-4-pyridylmethyl, N-2-picolyl N'-oxide or N-dibenzosuberyl groups), phosphinyl and phosphoryl groups (e.g. N-diphenylphosphinyl, N-dimethylthiophosphinyl, N-diphenylthiophosphinyl, N-diethylphosphoryl, N-dibenzylphosphoryl or N-phenylphosphoryl groups), sulfenyl groups (e.g. N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl or N-triphenylmethylsulfenyl groups), sulfonyl groups (e.g. N-benzenesulfonyl, N-p-methoxybenzenesulfonyl, N-2,4,6-trimethylbenzenesulfonyl, N-toluenesulfonyl, N-benzylsulfonyl, N-p-methylbenzylsulfonyl, N-trifluoromethylsulfonyl or N-phenacylsulfonyl) or the N-trimethylsilyl group.

The term "naturally occurring amino acid" as used herein includes the amino acids glycine, alanine, valine, leucine, isoleucine, phenylalanine, tryptophan, tyrosine, histidine, serine, threonine, methionine, cysteine, aspartic acid, glutamic acid, asparagine, glutamine, lysine, arginine and proline.

The term "pharmaceutically, or veterinarily, acceptable derivatives" includes non-toxic salts. Salts which may be mentioned include: acid addition salts, for example, salts formed with sulfuric, hydrochloric, hydrobromic, phosphoric, hydroiodic, sulfamic, organo-sulfonic, citric, carboxylic (e.g. acetic, benzoic, etc.), maleic, malic, succinic, tartaric, cinnamic, ascorbic and related acids; base addition salts; salts formed with bases, for example, the sodium, potassium and $C_{1-4}$ alkyl ammonium salts.

The compounds of the invention may also be in the form of quaternary ammonium salts, e.g. at the piperdine moiety, which salts may be formed by reaction with a variety of alkylating agents, such as an alkyl halide or an ester of sulfuric, or an aromatic sulfonic acid.

The compounds of the invention may exhibit tautomerism. All tautomneric forms of the compounds of formula I are included within the scope of the invention.

The compounds of the invention contain one or more asymmetric centres and thus they can exist as enantiomers and diastereomers is Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. The invention includes the use of both the separated individual isomers as well as mixtures of isomers. Also included within the scope of the invention are radiolabelled derivatives of compounds of formula I which are suitable for biological studies.

According to a further aspect of the invention, there is provided a compound of formula I, as hereinbefore defined, provided that when OY is attached in the meta- position relative to the piperidine ring, Y represents $R^{11}$, $R^{11}$ represents 2-(2-methyl)propionamide and the piperidine ring is not in N-oxidised form, then $R^3$ represents:

optionally substituted aryl;

optionally substituted $C_{3-10}$ alkenyl or $C_{3-10}$ alkynyl (which two groups are both interrupted by at least one oxygen and/or sulfur atoms);

$C_{2-10}$ alkyl, interrupted by at least two oxygen atoms and/or at least one sulfur atom;

$C_{1-10}$ alkyl, $C_{3-10}$ alkenyl or $C_{3-10}$ alkynyl, which groups are all optionally interrupted by one or more oxygen and/or sulfur atoms, and are substituted and/or terminated by one or more of:

$S(O)_n R^{4d}$, $N(R^{5a})S(O)_2 R^6$, $Het^1$ (substituted by one or more substituents selected from nitro, amino and $C_{1-5}$ alkanoyl (which latter group is optionally substituted by one or more halo atoms)), aryl (substituted by one or more substituents selected from nitro, amino and $C_{1-5}$ haloalkanoyl) or adamantyl (which latter group is substituted by one or more of the relevant substituents identified hereinbefore); or $OR^{4c}$, in which $R^{4c}$ represents $C_{7-10}$ alkyl, $C_{3-10}$ alkenyl, $C_{3-10}$ alkynyl or $Het^2$ (which latter four groups are all optionally substituted by one or more of the relevant substituents identified hereinbefore), or $R^{4c}$ represents $C_{1-10}$ alkyl, $C_{1-4}$ alkylphenyl, $C_{3-8}$ cycloalkyl or aryl (which latter four groups are all substituted by one or more of the relevant substituents identified hereinbefore);

-W-$A^1$-N($R^{5b}$)($R^{5c}$), in which $R^{5b}$ and/or $R^{5c}$ independently represent $C_{1-4}$ alkylphenyl (which latter group is optionally substituted by one or more of the relevant substituents identified hereinbefore), $C_{1-10}$ alkyl, $C_{3-10}$ alkenyl, $C_{3-10}$ alkynyl, $C_{3-8}$ cycloalkyl (which latter four groups are all substituted by one or more of the relevant substituents identified hereinbefore), or aryl (substituted by one or more substituents selected from nitro, amino and $C_{1-5}$ haloalkanoyl);

which compounds may also be termed "compounds of the invention".

Preferred compounds of the invention include those wherein:

The group OY is attached to the benzene ring in the position meta- relative to the piperidine group;

$R^1$ represents $C_{1-2}$ alkyl;

$R^2$ represents H or $C_{1-2}$ alkyl;

$R^3$ represents $C_{1-6}$ alkyl, $C_{3-6}$ alkenyl or $C_{3-6}$ alklynyl wherein said alkyl, alkenyl or alkynyl groups are optionally substituted and/or terminated by one or more substituents selected from $OR^{4c}$, CN, halo, $Het^1$ or aryl (which latter group is optionally substituted by one or more substituents selected from OH, $C_{1-2}$ alkyl, $C_{1-2}$ alkoxy or halo);

$R^{4c}$ represents H, $C_{1-6}$ alkyl, $C_{4-6}$ cycloalkyl, aryl or $Het^2$;

$Het^1$ and $Het^2$ independently represent 5- to 7-membered heterocyclic groups, which groups contain at least one heteroatom selected from oxygen, sulfur and/or nitrogen, and which groups are optionally substituted by one or more $C_{1-2}$ alkyl groups (which alkyl groups are optionally substituted by one or more halo atoms);

Y represents $C(=E)NR^8R^9$, $C(O)R^{10}$ or $R^{11}$;

$R^8$ and $R^9$ independently represent H or $C_{1-4}$ alkyl;

$R^{10}$ represents $C_{1-6}$ alkyl (substituted by one or more phenyl groups) or aryl (optionally substituted by one or more substituents selected from OH, halo, $C_{1-3}$ alkanoyloxy, $NH_2$, $C(O)NH_2$ and $C_{1-3}$ alkyl (which latter group is optionally substituted by one or more halo atoms));

$R^{11}$ represents $C_{1-5}$ alkyl (substituted by one or more substituents selected from $C(O)NH_2$, $Het^8$, aryl and aryloxy), $C_{6-10}$ alkyl or $C_{3-10}$ alkenyl, which latter two groups are optionally substituted by one or more substituents selected from $Het^6$ and aryl;

$Het^6$ and $Het^8$ independently represent 5- to 6-membered heterocyclic rings, which rings contain at least one heteroatom selected from oxygen, sulfur and/or nitrogen, which rings are optionally fused to a benzene ring, and which rings are optionally substituted in the heterocyclic and/or fused benzene ring part by one or more substituents selected from OH, =O and $C_{1-4}$ alkyl);

$Het^6$ and $Het^8$ are in S-oxidised form.

More preferred compounds of the invention include those wherein:

$R^1$ represents methyl;

$R^2$ represents H or methyl;

$R^3$ represents linear, saturated $C_{1-6}$ alkyl optionally substituted and/or terminated by one or more substituents selected from $OR^{4c}$ or $Het^1$;

$R^{4c}$ represents $C_{1-6}$ alkyl or $C_{4-6}$ cycloalkyl;

$Het^1$ represents a 5- or 6-membered saturated heterocyclic group, which groups contains one heteroatom selected from oxygen, sulfur or nitrogen; $R^8$ and $R^9$ independently represent H or $C_{1-3}$ alkyl;

$R^{10}$ represents $C_{1-4}$ alkyl (substituted by one or more phenyl groups) or phenyl (optionally substituted by one or more substituents selected from OH, $C_{1-2}$ alkanoyloxy, $NH_2$ and $C_{1-2}$ alkyl);.

$R^{11}$ represents linear or branched $C_{1-4}$ alkyl (substituted by one or more substituents selected from $C(O)NH_2$, phenyl and $Het^8$), $C_{6-8}$ alkyl or $C_{3-5}$ alkenyl;

$Het^8$ represents a 5-membered heterocyclic ring, which ring contains at least one heteroatom selected from oxygen, sulfur and/or nitrogen, which ring is fused to a benzene ring, and which ring is optionally substituted in the heterocyclic and/or fused benzene ring part by one or more substituents selected from =O and $C_{1-4}$ alkyl);

Particularly preferred compounds of the invention include those wherein: $R^1$ and $R^2$ represent methyl groups in the mutually Irans configuration.

Preferred compounds of the invention include the compounds of the Examples described hereinafter.

Thus, according to a further aspect of the invention, there is provided a compound of formula I which, irrespective of any of the foregoing definitions, is:

(±)-3-(1-hexyl-trans-3,4-dimethyl-4-piperidinyl)phenyl dimethylcarbamate;

(±)-3-(1-hexyl-trans-3,4-dimethyl-4-piperidinyl)phenyl methylcarbamate;

(±)-3-(1-hexyl-trans-3,4-dimethyl-4-piperidinyl)phenyl diethylcarbamate;

(±)-3-(1-hexyl-trans-3,4-dimethyl-4-piperidinyl)phenyl pivalate;

(±)-3-(1-hexyl-trans-3,4-dimethyl-4-piperidinyl)phenyl 2-(acetyloxy)benzoate;

(±)-3-(1-hexyl-trans-3,4-dimethyl-4-piperidinyl)phenyl salicylate;

2-{[(±)-3-(1-hexyl-trans-3,4-dimethyl-4-piperidinyl)-phenoxy]methyl}-1H-1,2-benzisothiazole-1,1,3(2H)-trione;

(±)-3-(1-hexyl-trans-3,4-dimethyl-4-piperidinyl)phenyl 2-methylbenzoate;

(±)-3-(1-hexyl-trans-3,4-dimethyl-4-piperidinyl)phenyl 2-aminobenzoate;

(±)-3-(1-hexyl-trans-3,4-dimethyl-4-piperidinyl)phenyl 2,6-dimethylbenzoate;

(±)-3-(1-hexyl-trans-3,4-dimethyl-4-piperidinyl)phenyl 2,2-diphenylpropionate;

(±)-2-{3-[1-(3-tetrahydro-2H-pyran-2-ylpropyl)-trans-3,4-dimethyl-4-piperidinyl]phenoxy}methyl-1H-1,2-benzisothiazole-1,1,3(2H)-trione;

(±)-3-[1-(3-tetrahydro-2H-pyran-2-ylpropyl)-trans-3,4-dimethyl-4-piperidinyl]phenyl 2-(acetyloxy)benzoate;

(±)-2-[(3-{1-[2-(cyclohexyloxy)ethyl]-trans-3,4-dimethyl-4-piperidinyl}phenoxy)methyl]-1H-1,2-benzisothiazole-1,1,3(2H)-trione;

(±)-3-{1-[2-(cyclohexyloxy)ethyl]-trans-3,4-dimethyl-4-piperidinyl}phenyl 2-(acetyloxy)benzoate;

(±)-4-(3-(1-carbamoyl-1-methylethoxy)phenyl)-N-hexyl-trans-3,4-dimethylpiperidine;

(±)-4-[3-(allyloxy)phenyl]-1-hexyl-trans-3,4-dimethylpiperidine;

(±)-O-[3-(1-hexyl-trans-3,4-dimethyl4-piperidinyl)phenyl] diethylcarbamothioate; or (±)-1-hexyl-trans-3,4-dimethyl-4-[3-(exyloxy)phenyl]piperidine, which compounds may also be termed "compounds of the invention".

According to a further aspect of the invention there is provided processes for the preparation of compounds of the invention, as illustrated below.

The following processes are illustrative of the general synthetic procedures which may be adopted in order to obtain the compounds of the invention.

1. Compounds of formula I wherein $R^3$ represents $C_1$ alkyl optionally substituted by $C_{3-8}$ cycloalkyl, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$, alkoxy and $C_{1-5}$ alkanoyl (which latter three groups are optionally substituted by one or more halo atoms)), or $R^3$ represents $C_{2-10}$ alkyl, $C_{3-10}$ alkenyl or $C_{3-10}$ alkynyl (which three groups are all optionally substituted by one or more of the relevant substituents identified hereinbefore in respect of $R^3$), which alkyl, alkenyl or alkynyl groups are attached to the piperidine nitrogen atom via a $CH_2$ group, wherein $Het^1$ is as hereinbefore defined, may be prepared by reduction of a corresponding compound of formula II,

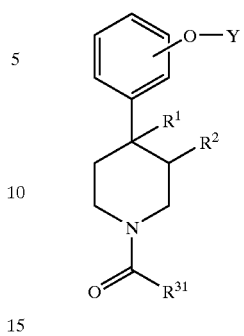

wherein $R^{31}$ represents H, $C_{3-8}$ cycloalkyl, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $-W-A^1-N(R^{5b})(R^{5c})$, and $R^1$, $R^2$, $R^{4c}$, $R^{4d}$, $R^{5a}$ to $R^{5c}$, $R^6$, $Het^1$, n, Y, W and $A^1$ are as hereinbefore defined, using a suitable reducing agent (e.g. lithium aluminium hydride or a borane derivative), for example as described hereinbefore.

Compounds of formula II may be prepared by reaction of a corresponding compound of formula III,

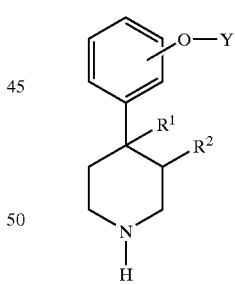

wherein $R^1$, $R^2$ and Y are as hereinbefore defined with a compound of is formula IV,

or a suitable (e.g. carboxylic acid) derivative thereof (e.g. an acid halide or anhydride), wherein $R^{31}$ is as hereinbefore defined, using coupling conditions known to those skilled in the art.

Compounds of formula III may be prepared from appropriate precursors by analogy with other methods disclosed herein that describe the production of compounds of formula I.

2. Compounds of formula I may be prepared by reaction of a corresponding compound of formula III, as hereinbefore defined, with a compound of formula V, $$R^3\text{-}L^1 \quad\quad V$$

wherein $L^1$ represents a leaving group (such as halo, alkanesulfonate, perfluoroalkanesulfonate or arenesulfonate) and $R^3$ is as hereinbefore defined, under conditions that are known to those skilled in the art, which include, for example, alkylation at between room temperature and reflux temperature in the presence of a reaction-inert organic solvent (e.g. N,N-dimethylformamide) and a suitable base (e.g. $NaHCO_3$), and arylation at between room temperature and reflux temperature in the presence of a suitable catalyst system (e.g. tris(dibenzylideneacetone)-palladium(0) combined with tri-o-tolylphosphine), an appropriate strong base (e.g. sodium tert-butoxide) and a reaction-inert solvent (e.g. toluene).

3. Compounds of formula I wherein $R^3$ represents $C_1$ alkyl, which, in place of being optionally substituted by the substituents as defined hereinbefore, is instead optionally substituted by $R^{31}$, wherein $R^{31}$ is as hereinbefore defined, may be prepared by reaction of a corresponding compound of formula III, as hereinbefore defined, with a compound of formula VI, $$R^{31}CHO \quad\quad VI$$

wherein $R^{31}$ is as hereinbefore defined, for example in the presence of a suitable reducing agent (e.g. sodium borohydride, sodium cyanoborohydride or sodium triacetoxyborohydride) and an appropriate solvent (e.g. methanol).

4. Compounds of formula I wherein $R^3$ is a $C_{1-10}$ alkyl, $C_{4-10}$ alkenyl or $C_{4-10}$ alkynyl group that is fully saturated from 1- to 3-C (relative to the piperidine N-atom), and which $R^3$ group is substituted at 2-C (relative to the piperidine N-atom) by $S(O)R^{4d}$, $S(O)_2R^{4d}$, alkanoyl, cycloalkanoyl, alkoxy carbonyl, CN, —C(O)-$A^1$-N($R^{5b}$)($R^{5c}$), —S(O)-$A^1$-N($R^{5b}$)($R^{4c}$), or —S(O)$_2$-$A^1$-N($R^{5b}$)($R^{5c}$), wherein $R^{4d}$, $R^{5b}$, $R^{5c}$ and $A^1$ are as hereinbefore defined, may be prepared by reaction of a corresponding compound of formula III, as hereinbefore defined, with a compound of formula VII, $$R^{3a}\text{-}Z \quad\quad VII$$

wherein $R^{3a}$ represents $R^3$ as hereinbefore defined except that it does not represent aryl, and that the $R^{3a}$ chain contains an additional carbon-carbon double bond α,β to the Z-substituent, and Z represents $S(O)R^{4d}$, $S(O)_2R^{4d}$, alkanoyl, cycloalkanoyl, alkoxy carbonyl, CN, —C(O)-$A^1$-N($R^{5b}$)($R^{5c}$), —S(O)-$A^1$-N($R^{5b}$)($R^{5c}$), or —S(O)$_2$-$A^1$-N($R^{5b}$)($R^{5c}$), wherein $R^{4d}$, $R^{5b}$, $R^{5c}$ and $A^1$ are as hereinbefore defined, for example at between room and reflux temperature in the presence of a reaction-inert solvent (e.g. THF).

5. Compounds of formula I in which Y represents —C(=E)$NR^8R^9$, wherein E, $R^8$ and $R^9$ are as hereinbefore defined, may be prepared by reaction of a corresponding compound of formula VIII,

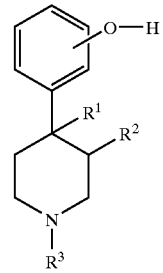

wherein $R^1$, $R^2$ and $R^3$ are as hereinbefore defined, with a compound of formula IX, $$HO\text{—}C(=E)NR^8R^9 \quad\quad IX,$$

or a suitable (e.g. carboxylic acid) derivative thereof (e.g. an acid chloride), wherein E, $R^8$ and $R^9$ are as hereinbefore defined, or a compound of formula X, $$E=C=NR^8R^9 \quad\quad X$$

wherein E, $R^8$ and $R^9$ are as hereinbefore defined, for example (in both cases) at between room and reflux temperature in the presence of a suitable base (e.g. KOH, triethylamine and/or pyridine) and optionally in the presence of an appropriate solvent (e.g. THF, water, or a suitable mixture thereof).

6. Compounds of formula I in which Y represents C(O)$R^{10}$ or C(O)O$R^{10a}$, wherein $R^{10}$ and $R^{10a}$ are as hereinbefore defined, may be prepared by reaction of a corresponding compound of formula VIII, as hereinbefore defined, with a compound of formula XI, $$HO\text{—}C(O)R^{10} \quad\quad XI,$$

or a compound of formula XII, $$HO\text{—}C(O)OR^{10a} \quad\quad XII$$

respectively, or suitable (e.g. carboxylic acid) derivatives thereof (e.g. acid halides or anhydrides), wherein $R^{10}$ and $R^{10a}$ are as hereinbefore defined, under coupling conditions known to those skilled in the art.

7. Compounds of formula I in which Y represents C(O)CH($R^{10b}$)N(G)($G^a$), wherein $R^{10b}$, G and $G^a$ are as hereinbefore defined may be prepared by reaction of a corresponding compound of formula VII, as hereinbefore defined, with a compound of formula XIII, $$HO\text{—}C(O)CH(R^{10b})N(G)(G^a) \quad\quad XIII$$

or a suitable (e.g. carboxylic acid) derivative thereof, wherein $R^{10b}$, G and $G^a$ are as hereinbefore defined, under coupling conditions known to those skilled in the art.

8. Compounds of formula I in which Y represents C(O)C($R^{13a}$)=C($R^{13b}$)$NH_2$ or C(O)CH($R^{13a}$)CH($NH_2$)($R^{13b}$), wherein $R^{13a}$ and $R^{13b}$ are as hereinbefore defined may be prepared by reaction of a corresponding compound of formula VIII, as hereinbefore defined, with a compound of formula XIV,

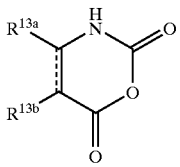

wherein the dashed line represents an optional double bond, and $R^{13a}$ and $R^{13b}$ are as hereinbefore defined, for example at between room and reflux temperature in the presence of a suitable solvent (e.g. N,N-dimethylformamide) and an appropriate base (e.g. N,N-dimethyl-4-aminopyridine).

9. Compounds of formula I in which Y represents C(O)$R^{10}$, wherein $R^{10}$ represents phenyl substituted in the ortho-position by an amino group, and optionally substituted by one or more further substituents selected from OH, halo, $C_{1-4}$ alkanoyl, $C_{1-4}$ alkanoyloxy, $N(R^8)(R^9)$, $C(O)N(R^8)(R^9)$, $C_{1-4}$ alkyl and $C_{1-4}$ alkoxy (which latter two groups are optionally substituted by one or more halo atoms), and $R^8$ and $R^9$ are as hereinbefore defined, may be prepared by reaction of a corresponding compound of formula VIII, as hereinbefore defined, with a compound of formula XV,

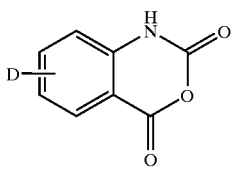

wherein D represents one to four optional substituents selected from OH, halo, $C_{1-4}$ alkanoyl, $C_{1-4}$ alkanoyloxy, $N(R^8)(R^9)$, $C(O)N(R^8)(R^9)$, $C_{1-4}$ alkyl and $C_{1-4}$ alkoxy (which latter two groups are optionally substituted by one or more halo atoms), and $R^8$ and $R^9$ are as hereinbefore defined, for example at between room and reflux temperature in the presence of a suitable solvent (e.g. N,N-dimethylformamide) and an appropriate base (e.g. N,N-dimethyl-4-aminopyridine).

10. Compounds of formula I in which Y represents $R^{11}$, wherein $R^{11}$ is as hereinbefore defined, may be prepared by reaction of a corresponding a compound of formula VIII, as hereinbefore defined, with a compound of formula XVI, $$R^{11}\text{-}L^2 \qquad \text{XVI}$$

wherein $L^2$ represents a leaving group such as halo, arenesulfonate, alkanesulfonate, perfluoroalkanesulfonate or diazo, and $R^{11}$ is as hereinbefore defined, for example under coupling conditions known to those skilled in the art (such as those described in respect of process 2 above).

11. Compounds of formula I in which Y represents $CH(R^{12b})C(O)OR^{12a}$ or $CH(R^{12b})OC(O)OR^{12a}$, wherein $R^{12a}$ and $R^{12b}$ are as hereinbefore defined, may be prepared by reaction of a corresponding compound of formula VIII, as hereinbefore defined, with a compound of formula XVII, $$L^2\text{-}CH(R^{12b})C(O)OR^{12a} \qquad \text{XVII}$$

or a compound of formula XVIII, $$L^2\text{-}CH(R^{12b})OC(O)OR^{12a} \qquad \text{XVIII}$$

wherein $R^{12a}$, $R^{12b}$ and $L^2$ are as hereinbefore defined, for example under coupling conditions known to those skilled in the art (such as those described in respect of process 2 above).

12. Compounds of formula I in which Y represents $PO(OR^{14})_2$, wherein $R^{14}$ is as hereinbefore defined, may be prepared by reaction of a compound of formula VIII, as hereinbefore defined, with a compound of formula XIX, $$H\text{—}PO(OR^{14})_2 \qquad \text{XIX}$$

or a compound of formula XX, $$HO\text{—}PO(OR^{14})_2 \qquad \text{XX}$$

or a suitable (e.g. phosphoric acid) derivative thereof (e.g. a pyrophosphate, cyanophosphate or chlorophosphate), wherein $R^{14}$ is as hereinbefore defined, for example at between −10° C. and reflux temperature in the presence of a suitable base (e.g. NaH, triethylamine) and an appropriate organic solvent (e.g. THF, dichloromethane or carbon tetrachloride).

Compounds of formulae IV to XX, and derivatives thereof, when not commercially available or not subsequently described, may be obtained either by analogy with the processes described herein, or by conventional synthetic procedures, in accordance with standard techniques, from readily available starting materials using appropriate reagents and reaction conditions (see, for example, "Comprehensive Organic Transformations—A Guide to Functional Group Preparations", R. C. Larrock, VCH (1989), or "Advanced Organic Chemistry—Reactions, Mechanism and Structure", 4$^{th}$ edition, J. March, Wiley-Interscience (1992)). For example, compounds of formula VIII may be made according to or by analogy with the procedures disclosed in the publications mentioned above relating to 4-arylpiperidine-based compounds.

Substituents on alkyl, heterocyclic and aryl groups in the above-mentioned compounds may also be introduced, removed and interconverted, using techniques which are well known to those skilled in the art. For example, nitro may be reduced to amino, OH may be alkylated to give alkoxy, alkoxy and alkanoyloxy may be hydrolysed to OH, alkenes may be hydrogenated to alkanes, halo may be hydrogenated to H, etc.

The skilled person will also appreciate that other various standard substituent or functional group interconversions and transformations within certain compounds of formula I will provide other compounds of formula I.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, OH, amino and carboxylic acid. Suitable protective groups for oxo include acetals, ketals (e.g. ethylene ketals) and dithianes. Suitable protective groups for OH include trialkylsilyl and diarylalylsilyl groups (e.g. tert-butyldimethylsilyl, tert-butyldiphenylsilyl or trimethylsilyl) and tetrahydropyranyl. Suitable protective groups for amino include tert-butyloxycarbonyl, 9-fluorenylmethoxycarbonyl or benzyloxycarbonyl. Suitable protective groups for carboxylic acid include $C_{1-6}$ alkyl or benzyl esters. Suitable protective groups for terminal alkynes include trialkylsilyl and diarylalkylsilyl groups (e.g. tert-butyldimethylsilyl, tert-butyldiphenylsilyl or trimethylsilyl).

The protection and deprotection of functional groups may take place before or after any of the reaction steps described hereinbefore.

Protective groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", $2^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

Pharmaceutically acceptable acid addition salts of the compounds of formula I which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The above procedures may be adapted as appropriate to the particular reactants and groups involved and other variants will be evident to the skilled chemist by reference to standard textbooks and to the examples provided hereafter to enable all of the compounds of formula I to be prepared.

Compounds of the invention may possess pharmacological activity as such.

Other compounds of formula I may not possess such activity per se, but may be administered parenterally or orally, and thereafter metabolised in the body to form compounds that are pharmacologically active. This may include compounds in which, in place of the group Y, an H is present. Such compounds (which also include compounds that may possess some pharmacological activity, but that activity is appreciably lower than that of the active compounds to which they are metabolised to), may therefore be described as "prodrugs".

Further, it will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may also therefore be described as "prodrugs".

Further, certain compounds of formula I may act as prodrugs of other compounds of formula I.

It will be further appreciated by those skilled in the art, that certain moieties, known to those skilled in the art as "pro-moieties", for example as described in 'Design of Prodrugs' by H. Bundgaard, Elsevier, 1985 (the disclosure in which document is hereby incorporated by reference), may be placed on appropriate functionalities, when such functionalities are present within compounds of formula I.

All protected derivatives, and prodrugs, of compounds of formula I are included within the scope of the invention.

The compounds of the invention are useful because they possess pharmacological activity, and/or are metabolised in the body following oral or parenteral administration to form compounds which possess pharmacological activity. The compounds of the invention are therefore indicated as pharmaceuticals and, in particular, for use as animal medicaments.

According to a further aspect of the invention there is provided the compounds of the invention for use as medicaments, such as pharmaceuticals and animal medicaments.

By the term "treatment", we include both therapeutic (curative) or prophylactic treatment.

In particular, the compounds of the invention have been found to be useful in the treatment of pruritus, and conditions characterised by pruritus as a symptom.

Thus, according to a further aspect of the invention there is provided the use of the compounds of the invention in the manufacture of a medicament for the treatment of pruritus or a medical condition characterised by pruritus as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing pruritus or a medical condition characterised by pruritus as a symptom in an animal (e.g. a mammal), which comprises administering a therapeutically effective amount of a compound of the invention to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, e.g. fipronil, lufenuron, imidacloprid, avermectins (e.g. abamectin, ivermectin, doramectin), milbemycins, organophosphates, pyrethroids; antihistamines, e.g. chlorpheniramine, trimeprazine, diphenhydramine, doxylamine; antifungals, e.g. fluconazole, ketoconazole, itraconazole, griseofulvin, amphotericin B; antibacterials, e.g. enroflaxacin, marbofloxacin, ampicillin, amoxycillin; anti-inflammatories e.g. prednisolone, betamethasone, dexamethasone, carprofen, ketoprofen; dietary supplements, e.g. gamma-linoleic acid; and emollients. Therefore, the invention further provides a product containing a compound of the invention and a compound from the above list as a combined preparation for simultaneous, separate or sequential use in the treatment of pruritus.

The skilled person will also be appreciated that compounds of the invention may be taken as a single dose on an "as required" basis (i.e. as needed or desired).

Thus, according to a further aspect of the invention there is provided a pharmaceutical, or veterinary, formulation including a compound of the invention in admixture with a pharmaceutically, or veterinarily, acceptable adjuvant, diluent or carrier.

Compounds of the invention may also have the advantage that, in the treatment of human and/or animal patients, they may be, or may be metabolised to form compounds that may be, more efficacious than, be less toxic than, have a broader range of activity than, be more potent than, produce fewer side effects than, be more easily absorbed than, or they may have other useful pharmacological properties over, compounds known in the prior art.

The biological activity of the compounds of the present invention was determined by the following test method.

Biological Test

The compounds of the invention are evaluated for their activity as antipruritic agents by measuring their ability to inhibit the hind leg scratching behaviour induced in rats by the administration of a known pruritogenic agent. These studies are based on the procedure described by Berendsen and Broekkamp in the European Journal of Pharmacology, 1991, 194, 201. The test is performed as follows:

Male Wistar rats (approximately 150 g body weight) are challenged with a pruritogen by subcutaneous injection of 5-methoxytryptamine hydrochloride (4 mg/3 mL/kg) dissolved in physiological saline into the scruff of the neck. At this dose a constant and quantifiable hindleg scratching response lasting up to 90 minutes is obtained.

The test compound is administered to the test animals by subcutaneous injection in an aqueous micelle formulation. The test compound is prepared in the following manner. The compound is dissolved in a vehicle (composition v/v %: glycerol formal, 24; tween 80, 17; benzyl alcohol, 1.5 and purified water to 100) then seven parts purified water is added to three parts of the above vehicle to give the aqueous micelle formulation. The compounds can be administered pre- or post-challenge or may be administered at the same time as the pruritogenic challenge.

After the pruritogen challenge has been administered, hindleg scratching is scored for each animal by recording the presence or absence of scratching during each 30 second interval as 1 or 0 scored respectively. The score for each animal is totalled after 25 minutes (maximum score 50). The efficacy of compounds is assessed by their ability to significantly reduce the score in treated groups compared to the control group.

The invention is illustrated by the following Preparations and Examples in which the following abbreviations may be used:

APCI=atmospheric pressure chemical ionisation
br (in relation to NMR)=broad
DMF=N,N-dimethylformamide
DMSO=dimethylsulfoxide
d (in relation to time)=day
d (in relation to NMR)=doublet
dd (in relation to NMR)=doublet of doublets
EtOAc=ethyl acetate
EtOH=ethanol
h=hour(s)
m (in relation to NMR)=multiplet
MeOH=methanol
min=minute
q (in relation to NMR)=quartet
s (in relation to NMR)=singlet
t (in relation to NMR)=triplet THF=tetrahydrofuran
TSI=thermospray ionisation When column chromatography is referred to this usually refers to a glass column packed with silica gel (40–63 μm). Pressure of about 165 kPa is generally applied and the ratio of crude product:silica gel required for purification is typically 50:1. Alternatively, an Isolute™ SPE (solid phase extraction) column or Waters Sep-Pak™ cartridge packed with silica gel may be used under atmospheric pressure. The ratio of crude product to silica gel required for purification is typically 100:1.

The hydrochloride salt may be made by methods commonly known to those skilled in the art of synthetic chemistry. Typically, a solution of the product in diethyl ether (10 mL/mmol) was added ethereal hydrogen chloride (1 M solution, 1 eq.) to afford a precipitate which was collected by filtration and dried in vacuo. Acetate salts can be prepared by similar methods, a typical example of which follows. To a solution of the product in methanol (5 ml/mmol) was added acetic acid (1 mol. eq.), after which the reaction mixture was concentrated in vacuo to afford the product.

Nuclear magnetic resonance (NMR) spectral data were obtained using a Varian Unity 300 or 400 spectrometer, the observed chemical shifts (δ) being consistent with the proposed structures. Mass spectral (MS) data were obtained on a Fisons Instruments Trio 1000, or a Fisons Instruments Trio 1000 APCI, or a Finnigan Navigator MS, or a Micromass Platform LC spectrometer. The calculated and observed ions quoted refer to the isotopic composition of lowest mass. HPLC means high performance liquid chromnatography. Room temperature means 20 to 25° C.

EXAMPLES

Example 1

(±)-3-(1-Hexyl-trans-3,4-dimethyl-4-piperidinyl) phenyl dimethylcarbamate

To a stirred solution of (±)-1-hexyl-trans-3,4-dimethyl-4-(3-hydroxyphenyl)piperidine (Preparation 1, 0.289 g, 1.00 mmol) and dimethylcarbamyl chloride (0.101 mL, 1.1 mmol) in tetrahydrofuran (2 mL) and pyridine (2 mL) was added triethylamine (0.279 mL, 2 mmol). After 24 h, the reaction mixture was diluted with water (20 mL) and extracted with dichloromethane (3×20 mL). The combined extracts were washed with brine (30 mL), dried ($Na_2SO_4$), filtered and concentrated in vacuo to give the crude product which was purified by silica gel chromatography, eluting with a gradient of methanol:dichloromethane:0.880 ammonia (10:989:1 to 30:967:3), to give the title compound as a yellow oil (0.329 g, 91%).

NMR ($C_6D_6$, selected data from the free base): 0.85 (t, 3H), 0.90 (d, 3H), 1.17 (s, 3H), 1.19–1.29 (m, 6H), 1.33–1.43 (m, 3H), 1.78 (m, 1H), 2.05–2.40 (m, 6H), 2.51 (s, 3H), 2.55 (s, 3H), 2.63 (m, 1H), 6.93 (m, 1H), 7.04–7.12 (m, 2H), 7.24 (m, 1H). MS ($APCI^+$): M/Z [$MH^+$] 361.3; $C_{22}H_{36}N_2O_2$+H requires 361.3.

Example 2

(±)-3-(1-Hexyl-trans-3,4-dimethyl-4-piperidinyl) phenyl methylcarbamate

To a stirred solution of (±)-1-hexyl-trans-3,4-dimethyl-4-(3-hydroxyphenyl)piperidine (Preparation 1, 0.029 g, 0.10 mmol) and methyl isocyanate (7 μL, 0.11 mmol) was added triethylamine (28 μL, 0.2 mmol) and the reaction was allowed to stir under reflux. After 5 h, additional methyl isocyanate (7 μL, 0.11 mmol) and triethylamine (28 μL, 0.2 mmol) was introduced and stirring was continued at reflux for 14 h. Upon cooling, the reaction mixture was concentrated in vacuo to give the crude product which was purified by silica gel chromatography, eluting with a gradient of methanol:dichloromethane:0.880 ammonia, (10:989:1 to 30:967:3), to give the title compound as a pale yellow oil (0.019 g, 55%).

NMR ($C_6D_6$, selected data from the free base): 0.86 (t, 3H), 0.91 (d, 3H), 1.18 (s, 3H), 1.24–1.43 (m, 9H), 1.78 (m, 1H), 2.06–2.42 (m, 9H), 2.65 (m, 1H), 4.05 (br, 1H), 6.94 (m, 1H), 7.04–7.12 (m, 2H), 7.26 (m, 1H). MS ($APCI^+$): M/Z [$MH^+$] 347.2; $C_{21}H_{34}N_2O_2$+H requires 347.3.

Example 3

(±)-3-(1-Hexyl-trans-3,4-dimethyl-4-piperidinyl) phenyl diethylcarbamate

To a stirred solution of (±)-1-hexyl-trans-3,4-dimethyl-4-(3-hydroxyphenyl)piperidine (Preparation 1, 0.145 g, 0.50 mmol) in pyridine (2 mL) was added diethylcarbamyl chloride (76 μL, 0.6 mmol). After 24 h, the reaction mixture was diluted with water (10 mL) and extracted with dichloromethane (3×20 mL). The combined extracts were washed with brine (30 mL), dried ($Na_2SO_4$), filtered and concentrated in vacuo to give the crude product which was purified by silica gel chromatography, eluting with a gradient of methanol:dichloromethane:0.880 ammonia (10:988:2 to 20:978:2), to give the title compound as a yellow oil (0.110 g, 57%).

NMR ($C_6D_6$, selected data from the free base): 0.78–0.92 (m, 12H), 1.17 (s, 3H), 1.20–1.41 (m, 9H), 1.77 (m, 1H), 2.03–2.40 (m, 6H), 2.63 (m, 1H), 3.02–3.11 (m, 4H), 6.94 (m, 1H), 7.04–7.12 (m, 21), 7.24 (m, 1H). MS ($APCI^+$): M/Z [$MH^+$] 389.3; $C_{24}H_{40}N_2O_2$+H requires 389.3.

Example 4

(±)-3-(1-Hexyl-trans-3,4-dimethyl-4-piperidinyl) phenyl pivalate

To a stirred solution of (±)-1-hexyl-trans-3,4-dimethyl-4-(3-hydroxyphenyl)piperidine (Preparation 1, 0.081 g, 0.30 mmol) in triethylamine (1.2 mL) and dichloromethane (1.8 mL) under nitrogen at 0° C. was added pivaloyl chloride (41 μL, 0.33 mmol) dropwise. The reaction mixture was stirred at room temperature overnight before being partitioned between saturated aqueous sodium hydrogencarbonate and dichloromethane. The aqueous layer was further extracted with dichloromethane. The combined organic extracts were dried ($Na_2SO_4$), concentrated and subjected to purification on silica gel by flash column chromatography, eluting with ethyl acetate:hexane:0.880 ammonia solution (30:70:1), to afford the title compound (0.10 g, 89%) which was subsequently converted to the hydrochloride salt.

NMR ($CDCl_3$, selected data from the hydrochloride salt): 0.9 (m, 3H), 1.35 (s, 9H), 6.9–7.4 (m, 4H), 11.55 (br, 0.5H), 12.3 (br, 0.5H). MS ($TSI^+$): M/Z [$MH^+$] 374.5; $C_{24}H_{39}NO_2$+H requires 374.3.

Example 5

(±)-3-(1-Hexyl-trans-3,4-dimethyl-4-piperidinyl) phenyl 2-(acetyloxy)benzoate

To a stirred solution of (±)-1-hexyl-trans-3,4-dimethyl-4-(3-hydroxyphenyl)piperidine (Preparation 1, 0.211 g, 0.728 mmol) in triethylamine (2.8 mL) and dichloromethane (4.2 mL) under nitrogen at 0° C. was added 2-(chlorocarbonyl) phenyl acetate (0.159 g, 0.80 mmol) portionwise. The reaction mixture was left to warm to room temperature overnight, before partitioning between aqueous 1 M sodium hydroxide solution and dichloromethane. The aqueous layer was then further extracted with dichloromethane. The combined organic extracts were dried ($Na_2SO_4$), concentrated and subjected to purification on silica gel using flash column chromatography, eluting with ethyl acetate:hexane:0.880 ammonia solution (15:85:1). The title compound was obtained as a clear oil (0.217 g, 66%) which was subsequently converted to the hydrochloride salt.

NMR ($CDCl_3$, selected data from the hydrochloride salt): 0.85 (m, 3H), 1.8–2.0 (m, 2H), 2.3 (s, 3H), 7.0–7.4 (m, 6H), 7.7 (m, 1H), 8.2 (m, 1H), 11.5 (br, 0.4H), 12.25 (br, 0.6H). MS ($TSI^+$): M/Z [$MH^+$] 452.3; $C_{28}H_{37}NO_4$+H requires 452.3.

Example 6

(±)-3-(1-Hexyl-trans-3,4-dimethyl-4-piperidinyl) phenyl salicylate

A solution of 3-(1-hexyl-trans-3,4-dimethyl-4-piperidinyl)phenyl 2-(acetyloxy)benzoate (Example 5, 0.146 g, 0.3 mmol) in concentrated hydrochloric acid (0.5 mL) and methanol (9.5 mL) was stirred at room temperature overnight. The reaction mixture was concentrated, partitioned between dichloromethane (50 mL) and water (15 mL), and the resulting aqueous layer adjusted to pH 8 with 0.880 ammonia solution. The phases were separated and the aqueous layer was further extracted with dichloromethane (2×15 mL). The combined organic extracts were washed with water (20 mL), dried ($Na_2SO_4$) and concentrated to afford a crude oil. The crude oil was purified using flash column chromatography, eluting with ethyl acetate:hexane:0.880 ammonia solution (25:75:1), to give an oil which was converted into its hydrochloride salt (110 mg, 82%).

NMR ($CDCl_3$, selected data from the hydrochloride salt): 0.9 (m, 3H), 1.8–2.0 (m, 2H), 2.2 (m, 1H), 6.9–7.6 (m, 7H), 8.05 (d, 1H), 11.55 (br, 0.8H), 12.3 (br, 0.2H). MS ($TSI^+$): M/Z [$MH^+$] 410.7; $C_{26}H_{35}NO_3$+H requires 410.3.

Example 7

2-{[(±)-3-(1-Hexyl-trans-3,4-dimethyl-4-piperidinyl)-phenoxy]methyl}-1H-1,2-benzisothiazole-1,1,3(2H)-trione A mixture of (±)-1-hexyl-trans-3,4-dimethyl-4-(3-hydroxyphenyl)piperidine (Preparation 1, 0.122 g, 0.42 mmol), sodium iodide (0.063 g, 0.42 mmol), potassium carbonate (0.06 g, 0.42 mmol) and N-(chioromethyl)saccharin (Reference 1, 98 mg, 0.42 mmol) in acetone (4 mL) was stirred under nitrogen at room temperature overnight. The reaction mixture was filtered through a plug of cotton wool, concentrated and subjected directly to flash column chromatography on silica gel, eluting with ethyl acetate: hexane:0.880 ammonia solution (30:70:1), to afford the title compound as a clear oil which was subsequently converted to the hydrochloride salt (125 mg, 57%).

NMR ($CDCl_3$, selected data from the hydrochloride salt): 0.8 (m, 6H), 1.8–2.0 (m, 2H), 2.2 (m, 1H), 5.8 (br, 2H), 7.0–7.4 (m, 4H), 7.8–8.2 (m, 4H), 11.45 (br, 0.33H), 12.1 (br, 0.67H). MS ($TSI^+$): M/Z [$MH^+$] 485.3; $C_{27}H_{36}N_2O_4S$+H requires 485.2.

Example 8

(±)-3-(1-Hexyl-trans-3,4-dimethyl-4-piperidinyl) phenyl 2-methylbenzoate

To a stirred solution of (±)-1-hexyl-trans-3,4-dimethyl-4-(3-hydroxyphenyl)piperidine (Preparation 1, 0.089 g, 0.307 mmol) in dichloromethane (1.8 mL) and triethylamine (1.2 mL) at 0° C. under nitrogen, was added o-toluoyl chloride (45 μL, 0.34 mmol) dropwise. The reaction mixture was stirred at room temperature for 2½ days. The reaction mixture was diluted with water (25 mL) and extracted with dichloromethane (50 mL followed by 2×25 mL). The organic extracts were washed with water (20 mL), dried ($Na_2SO_4$) and subjected to flash column chromatography, eluting ethyl acetate:hexane:0.880 ammonia solution (30:70:1), to afford the title compound as an oil (0.095 g, 76%) which was subsequently converted into the hydrochloride salt.

NMR ($CDCl_3$, selected data from the hydrochloride salt): 0.85 (m, 3H), 1.8–2.0 (m, 2H), 2.2 (m, 1H), 2.6 (s, 3H), 7.0–7.6 (m, 7H), 8.15 (d, 1H), 11.65 (br, 0.4H), 12.4 (br, 0.6H). MS ($TSI^+$): M/Z [$MH^+$] 408.6; $C_{27}H_{37}NO_2$+H requires 408.3.

Example 9

(±)-3-(1-Hexyl-trans-3,4-dimethyl-4-piperidinyl) phenyl 2-aminobenzoate

A stirred solution of (±)-1-bexyl-trans-3,4-dimethyl-4-(3-hydroxyphenyl)piperidine (Preparation 1, 0.069 g, 0.238 mmol), 4-(dimethylamino)pyridine (0.032 g, 0.262 mmol) and isatoic anhydride (0.043 g, 0.262 mmol) in N,N-dimethylformamide (2 mL) was heated for 12 hours at 80° C. under nitrogen. The reaction mixture was diluted with water (25 mL) and the product was extracted with dichloromethane (50 mL followed by 2×25 mL). The combined organic extracts were washed with water (20 mL), dried ($Na_2SO_4$) and concentrated in vacuo. The crude residue so obtained was subjected to flash column chromatography, eluting with ethyl acetate:hexane:0.880 ammonia solution (25:75:1), to afford the title compound as an oil (77 mg, 79%) which was subsequently converted to the hydrochloride salt.

NMR ($CDCl_3$, selected data from the hydrochloride salt): 0.8 (m, 3H), 1.8–2.0 (m, 2H), 2.25 (m, 1H), 5.6–5.8 (m, 2H), 6.65–6.7 (m, 2H), 7.0–7.2 (m, 3H), 7.3–7.4 (m, 2H), 8.05 (m, 1H), 11.6 (br, 0.35H), 12.3 (br, 0.65H). MS ($TSI^+$): M/Z [$MH^+$] 408.7; $C_{26}H_{36}N_2O_2$+H requires 409.3.

Example 10

(±)-3-(1-Hexyl-trans-3,4-dimethyl-4-piperidinyl) phenyl 2,6-dinethylbenzoate

To a solution of 2,6-dimethylbenzoic acid (0.092 g, 0.612 mmol) in dichloromethane (3.6 mL) stirred under nitrogen at 0° C., was added oxalyl chloride (54 µL, 0.612 mmol) followed by a catalytic amount of N,N-dimethylformamide (1 drop). This reaction mixture was stirred for 1½ hours before being added to a solution of (±)-1-hexyl-trans-3,4-dimethyl4-(3-hydroxyphenyl)piperidine (Preparation 1, 0.161 g, 0.556 mmol) in dichloromethane (1.5 mL). The combined reaction mixture was stirred under nitrogen at room temperature overnight. The reaction mixture was diluted with water (15 mL) and extracted with dichloromethane (2×20 mL). The combined organic extracts were dried ($Na_2SO_4$) and concentrated in vacua. The crude residue was purified by flash column chromatography on silica gel, eluting with ethyl acetate:hexane:0.880 ammonia solution (30:70:1), to give the title compound as a clear oil (0.157 g, 68%) which was subsequently converted into the hydrochloride salt.

NMR ($CDCl_3$, selected data from the hydrochloride salt): 0.75–0.9 (m, 6H), 1.8–1.9 (m, 2H), 2.2 (m, 1H), 2.4 (s, 6H), 7.0–7.4 (m, 7H), 11.6 (br, 0.45H), 12.3 (br, 0.55H). MS ($TSI^+$): M/Z [$MH^+$] 422.0; $C_{28}H_{39}NO_2$+H requires 422.3.

Example 11

(±)-3-(1-Hexyl-trans-3,4-dimethyl-4-piperidinyl) phenyl 2,2-diphenylpropionate

To a stirred mixture of 2,2diphenylpropionic acid (0.161 g, 0.711 mmol) in dichloromethane (4.2 mL) under nitrogen at 0° C., was added oxalyl chloride (62 µL, 0.711 mmol) followed by catalytic N,N-dimethylformamide (1 drop). After 1 hour, N,N-dimethylformamide (1 drop) was added, and the reaction mixture was warmed to 10° C. in order to improve the solubility of the acid. This reaction mixture was added to a solution of (±)-1-hexyl-trans-3,4-dimethyl-4-(3-hydroxyphenyl)piperidine (Preparation 1, 0.187 mg, 0.646 mmol) in triethylamine (2.8 mL) and dichloromethane (1.75 mL) at 0° C., and stirred under nitrogen overnight. The reaction mixture was diluted with water (15 mL) and extracted with dichloromethane (3×20 mL). The combined organic extracts were dried ($Na_2SO_4$) and concentrated in vacuo. The crude residue was purified on silica gel by flash column chromatography, eluting with ethyl acetate:hexane: 0.880 ammonia solution (25:75:1), to give the title compound as a clear oil (121 mg, 38%) which was subsequently converted to the hydrochloride salt.

NMR ($CDCl_3$, selected data from the hydrochloride salt): 0.85 (m, 3H), 1.8–2.0 (m, 2H), 2.0 (s, 3H), 6.8–6.95 (m, 4H), 7.05–7.20 (m, 2H), 7.25–7.4 (m, 8H), 11.65 (br, 0.33H), 12.35 (br, 0.67H). MS ($TSI^+$): M/Z [$MH^+$] 498.4; $C_{34}H_{43}NO_2$+H requires 498.3.

Example 12

(±)-2-{3-[1-(3-Tetrahydro-2H-pyran-2-ylpropyl)-trans-3,4-dimetbyl-4-piperidinyl]phenoxy}methyl-1H-1,2benzisothiazole-1,1,3(2H)-trione To a stirred solution of 3-[1-(3-tetrahydro-2H-pyran-2-ylpropyl)-trans-3,4-dimethyl-4-piperidinyl]phenol (Preparation 2, 7.589 g, 22.86 mmol) and sodium iodide (0.41 g, 2.74 mmol) in anhydrous acetone (100 mL) under nitrogen was added potassium carbonate (3.79 g, 27.43 mmol) followed by N-(chloromethyl)saccharin (Reference 1, 6.41 g, 27.43 mmol). The reaction mixture was stirred at room temperature overnight. The reaction mixture was filtered through Celite® and the filtrate was concentrated in vacuo. The crude residue so obtained was purified by flash column chromatography on silica gel, eluting with dichloromethane: ethanol:0.880 ammonia solution (200:8:1), to yield the title compound as an oil which solidified under reduced pressure (5.51 g, 46%). The hydrochloride salt was subsequently prepared as a white solid (5.62 g, 44%).

NMR ($CDCl_3$, selected data from the hydrochloride salt): 1.0 (m, 3H), 1.9–2.1 (m, 2H), 3.95 (m, 1H), 5.75–5.85 (br, 2H), 6.9–7.1 (m, 3H), 7.25 (m, 1H), 7.8–7.95 (m, 3H), 8.1 (m, 1H), 11.4 (br, 0.7H), 12.1 (br, 0.3H). MS ($TSI^+$): M/Z [$MH^+$] 527.7; $C_{29}H_{38}N_2O_5S$+H requires 527.3.

Example 13

(±)-3-[1-(3-Tetrahydro-2H-pyran-2-ylpropyl)-trans-3,4-dimethyl-4-piperidinyl]phenyl 2-(acetyloxy) benzoate To a stirred solution of 3-[1-(3-tetrahydro-2H-pyran-2-ylpropyl)-trans-3,4-dimethyl-4-piperidinyl]phenol (Preparation 2, 8.22 g, 24.75 mmol) in triethylamine (20 mL) and dichloromethane (80 mL) at 0° C. under nitrogen was added 2-(chlorocarbonyl)phenyl acetate (5.90 g, 29.71 mmol) portionwise. After 3 hours, the reaction mixture was quenched with ice (100 g), and after a further 1 hour, the organic and aqueous phases were separated. The aqueous layer was re-extracted with dichloromethane and the combined organic layers were dried ($Na_2SO_4$) and concentrated to afford a crude oil. The title compound was then obtained through purification by flash column chromatography on silica gel, eluting with dichloromethane:ethanol:0.880 anunonia solution (97:3:1). The hydrochloride salt (8.72 g, 66%) was subsequently prepared as a white solid (m.p. 79–80° C.).

NMR ($CDCl_3$, selected data from the hydrochloride salt): 1.1 (m, 3H), 1.4 (s, 3H), 2.0–2.1 (m, 2H), 2.3 (s, 3H), 3.65 (m, 1H), 3.95 (m, 1H), 7.0–7.4 (m, 6H), 7.6 (m, 1H), 8.2 (m, 1H), 11.5 (br, 0.8H), 12.2 (br, 0.2H). MS ($TSI^+$): M/Z [$MH^+$] 494.7; $C_{30}H_{39}NO_5$+H requires 494.3.

Example 14

(±)-2-[(3-{1-[2-(Cyclohexyloxy)ethyl]-trans-3,4-dimethyl-4-piperidinyl}phenoxy)methyl]-1H-1,2-benzisothiazole-1,1,3(2H)-trione A solution of 3-{1-[2-(cyclohexyloxy)ethyl]-trans-3,4-dimethyl-4-piperidinyl}phenol (Preparation 6, 0.80 g, 2.41 mmol) and sodium iodide (0.43 g, 2.9 mmol) in anhydrous acetone (25 mL) was stirred under nitrogen. Potassium carbonate (1.66 g, 13.2 mmol) was added, followed by N-(chloromethyl)saccharin (Reference 1, 0.67 g, 2.9 mmol), and the reaction mixture was allowed to stir overnight at room temperature. The reaction mixture was filtered through a plug of Celite® and then concentrated in vacuo. The crude residue was purified by flash chromatography on silica gel, eluting with dichloromethane:0.880 ammonia (99:1), to yield the title compound (0.3 g, 24%).

NMR ($CDCl_3$, selected data from the free base): 0.75 (d, 3H), 1.15–2.35 (m, 9H), 2.8 (m, 1H), 3.2 (m, 1H), 3.55–3.65 (m, 2H), 6.9–7.0 (m, 2H), 7.05 (s, 1H), 7.25 (m, 1H), 7.8–8.0 (m, 3H), 8.1 (m, 1H). MS ($TSI^+$): M/Z [$MH^+$] 527.2; $C_{29}H_{38}N_2O_5S$+H requires 527.3.

Example 15

(±)-3-{1-[2-(Cyclohexyloxy)ethyl]-trans-3,4-dimethyl-4-piperidinyl}phenyl 2-(acetyloxy)benzoate A solution of 3-{1-[2-(cyclohexyloxy)ethyl]-trans-3,4-dimethyl-4-piperidinyl}phenol (Preparation 6, 0.80 g, 2.41 mmol) and sodium iodide (0.43 g, 2.9 mmol) in anhydrous acetone (25 mL) was stirred under nitrogen. Potassium carbonate (1.66 g, 13.2 mmol) was added followed by 2-(chlorocarbonyl)phenyl acetate (0.67 g, 2.9 mmol) and pyridine (9 mL), the reaction mixture was allowed to stir for 5 h at room temperature. The reaction mixture was diluted with dichloromethane (30 mL) and washed with water (30 mL), and the organic extract was washed with brine (20 mL), dried ($MgSO_4$), and concentrated in vacuo to give a yellow foam. This crude residue was partially purified by flash column chromatography on silica gel, eluting with $CH_2Cl_2$:0.880 ammonia (99:1) and then with $CH_2Cl_2$:ethanol:0.880 ammonia (75:25:1). Further purification of the product was effected by flash column chromatography on silica gel, eluting with a gradient of ethyl acetate:hexane:0.880 ammonia (10:90:1 and then 30:70:1), to yield the title compound (0.09 g, 8%).

NMR ($CDCl_3$, selected data from the free base): 0.8 (d, 3H), 1.4 (s, 3H), 2.3 (s, 3H), 2.85 (m, 1H), 3.25 (m, 1H), 3.55–3.65 (m, 2H), 7.0 (d, 1H), 7.1 (s, 1H), 7.15–7.25 (m, 2H), 7.3–7.4 (m, 2H), 7.6 (m, 1H), 8.2 (d, 1H). MS ($TSI^+$): M/Z [$MH^+$] 494.3; $C_{30}H_{39}NO_5$+H requires 494.3.

Example 16

(±)-4-(3-(1-Carbamoyl-1-methylethoxy)phenyl)-N-hexyl-trans-3,4-dimethylpiperidine To a solution of (±)-1-hexyl-trans-3,4dimethyl-4-(3-hydroxyphenyl)piperidine (Preparation 1, 20 g, 69.2 mmol) in 1,4dioxan (250 mL) under an atmosphere of nitrogen was added caesium carbonate (32.5 g, 100 mmol) carefully followed by sodium hydride (60% dispersion in mineral oil, 4 g, 100 mmol) in four portions over 30 min. The resultant mixture was stirred for 30 min before 2-bromo-2-methylpropionamide (Reference 2, 16.6 g, 100 mmol) was added, and the mixture was heated under reflux overnight. The reaction mixture was cooled, filtered and concentrated in vacuo to give the crude product which was purified by flash column chromatography on silica gel (600 g), eluting with a gradient of ethyl acetate:hexane:0.880 ammonia (30:70:1 to 50:50:1), to give recovered starting phenol (5.9 g, 30%), followed by the title compound as a white solid (14.3 g, 55%).

NMR ($CDCl_3$, selected data from the free base): 0.75 (d, 3H), 0.85 (m, 3H), 2.0 (m, 1H), 2.3 (m, 4H), 2.5 (m, 2H), 2.8 (m, 1H), 5.45 (br. s, 1H), 6.65 (br. s, 1H), 6.75–7.2 (m, 4H). MS ($TSI^+$): M/Z [$MH^+$] 375.4; $C_{23}H_{38}N_2O_2$+H requires 375.3.

Example 17

(±)-4-[3-(Allyloxy)phenyl]-1-hexyl-trans-3,4-dimethyl-piperidine

To a stirred solution of (±)-1-hexyl-trans-3,4-dimethyl-4-(3-hydroxyphenyl)piperidine (Preparation 1, 0.043 g, 0.15 mmol) and allyl bromide (15 µL, 0.017 mmol) in acetonitrile (3 mL) was added caesium carbonate (0.098 g, 0.3 mmol) and the reaction was heated under reflux for 6 h. Upon cooling, the reaction mixture was diluted with saturated aqueous sodium hydrogencarbonate (20 mL) and extracted with dichloromethane (3×20 mL). The combined organic extracts were washed with brine (25 mL), dried ($Na_2SO_4$), filtered and concentrated in vacuo to give the crude product which was purified by silica gel chromatography, eluting with a gradient of methanol:$CH_2Cl_2$:0.880 ammonia (10:989:1 to 30:967:3), to give the title compound as a yellow oil (0.031 g, 63%).

NMR ($C_6D_6$, selected data from the free base): 0.86 (t, 3H), 0.94 (d, 3H), 1.23 (s, 3H), 1.21–1.33 (m, 6H), 1.39–1.46 (m, 3H), 1.84 (m, 1H), 2.10–2.47 (m, 6H), 2.69 (m, 1H), 4.17–4.22 (m, 2H), 5.01 (m, 1H), 5.23 (m, 1H), 5.78–5.87 (m, 1H), 6.63 (dd, 1H), 6.83 (d, 1H), 6.99 (m, 1H), 7.14 (m, 1H). MS ($APCI^+$): M/Z [$MH^+$] 330.2; $C_{22}H_{35}NO$+H requires 330.3.

Example 18

(±)-O-[3-(1-Hexyl-trans-3,4-dimethyl-4-piperidinyl)phenyl]diethylcarbamothioate

To a stirred solution of (±)-1-hexyl-trans-3,4-dimethyl-4-(3-hydroxyphenyl)piperidine (Preparation 1, 0.710 g, 2.45 mmol) and potassium hydroxide (0.137 g, 2.45 mmol) in water (5 mL) and tetrahydrofuran (5 mL) was added diethylthiocarbamyl chloride (0.485 g, 3.2 mmol). After 24 h, additional potassium hydroxide (0.137 g, 2.45 mmol) and diethylthiocarbamyl chloride (0.485 g, 3.2 mmol) were introduced. After an additional 24 h, the reaction mixture was diluted with water (20 mL) and extracted with ethyl acetate (3×25 mL). The combined extracts were washed with brine (30 mL), dried ($Na_2SO_4$), filtered and concentrated in vacuo to give the crude product which was purified by silica gel chromatography, eluting with a gradient of methanol:dichloromethane:0.880 ammonia (10:989:1 to 30:967:3), to give the title compound as a yellow oil (0.627 g, 63%).

NMR ($C_6D_6$, selected data from the free base): 0.83–0.88 (m, 6H), 0.95–1.01 (m, 6H), 1.20 (s, 3H), 1.23–1.42 (m, 9H), 1.77 (m, 1H), 2.05–2.42 (m, 6H), 2.64 (m, 1H), 3.10 (q, 2H), 3.55 (q, 2H), 6.91 (m, 1H), 6.98 (m, 1H), 7.05–7.13 (m, 1H), 7.19 (m, 1H). MS ($APCI^+$): M/Z [$MH^+$] 405.3; $C_{24}H_{40}N_2OS$+H requires 405.3.

Example 19

(±)-1-Hexyl-trans-3,4-dimethyl-4-[3-(hexyloxy)phenyl]piperidine

To a solution of the acetate salt of (±)-3-(trans-3,4-dimethylpiperidinyl)phenol (Reference 3, 45 g, 170 mmol) in N,N-dimethylformamide (250 mL) and bromohexane (71.6 mL, 510 mmol) was added potassium carbonate (70.5 g, 510 mmol). The reaction mixture was stirred overnight at 50° C. The reaction mixture was diluted with water (500 mL) and extracted with ethyl acetate (3×200 mL), the combined extracts were washed with water (100 mL), dried ($MgSO_4$) and concentrated in vacao. The crude residue contained two products which were separated by flash column chromatography on silica gel, eluting with ethyl acetate:hexane:0.88 ammonia solution (10:90:1 and then 40:60:1). The title compound was obtained first, (1.2 g, 2%) followed by (±)-1-hexyl-trans-3,4-dimethyl4-(3-hydroxyphenyl)piperidine (13.6 g, 28%). MS ($TSI^+$): M/Z [$MH^+$] 374.4; $C_{25}H_{43}NO$+H requires 374.3.

Example 20

Compounds according to the present invention, for example the compound of Example 2, were found to display anti-pruritic activity when tested in accordance with the above procedure.

Preparation of Starting Materials

Preparation 1: (±)-1-Hexyl-trans-3,4-dimethyl-4-(3-hydroxyphenyl)piperidine

To a stirred solution of (±)-3-(trans-3,4-dimethylpiperidinyl)phenol (Reference 3, 2.0 g, 9.8 mmol) in N,N-dimethylformamide (50 mL) was added sodium hydrogencarbonate (1.76 g, 20.95 mmol) and bromohexane (1.64 g, 9.9 mmol). The reaction mixture was heated under reflux for 3 h and then cooled to room temperature. The reaction mixture was diluted with water (100 mL) and extracted with dichloromethane (4×50 mL). The combined extracts were washed with brine (100 mL), dried (MgSO$_4$), filtered and concentrated in vacuo to give the crude product. This was purified by silica (50 g) column chromatography, eluting with ethyl acetate:hexane:0.880 ammonia (30:70:1), to give the title compound as a light brown oil (2.68 g, 91%).

NMR (CDCl$_3$, selected data from the free base): 0.75 (d, 3H), 0.85 (t, 3H), 1.15–1.25 (m, 6H), 1.3 (s, 3H), 2.0 (m, 1H), 2.35 (m, 4H), 2.6 (m, 2H), 6.55–7.2 (m, 4H). MS (TSI$^+$): M/Z [MH$^+$] 290.2; C$_{19}$H$_{31}$NO+H requires 290.3.

Preparation 2: (±)-3-[1-(3-Tetrahydro-2H-pyran-2-ylpropyl)-trans-3,4-dimethyl-4-piperidinyl]phenol To a stirred solution of (±)-1-[trans-3,4-dimethyl-4-(3-hydroxyphenyl)-1-piperidinyl]-3-tetrahydro-2H-pyran-2-yl-1-propanone (Preparation 3, 0.470 g, 1.36 mmol) in diethyl ether (6.6 mL) at room temperature was added lithium aluminium hydride (2.72 mL of 1.0 M in diethyl ether, 2.72 mmol). After 2 hours, the reaction was quenched with aqueous 2N sodium hydroxide solution (0.2 μL) and water (0.3 μL) and diluted with diethyl ether (15 mL). The solid was then removed by filtration through Celite®, washing with ethyl acetate (5×50 mL). The filtrate was dried (Na$_2$SO$_4$), filtered and concentrated in vacuo to give the title compound (396 mg, 88%) as a pale yellow oil.

NMR (CDCl$_3$, data from the free base): 0.78 (d, 3H), 1.38 (s, 3H), 1.80 (m, 1H), 1.95 (m, 1H), 2.20–2.70 (m, 5H), 2.78–2.90 (m, 1H), 3.25 (m, 1H), 3.41(m, 1H), 3.98 (m, 1H), 6.65 (d, 1H), 6.75 (s, 1H), 6.82 (d, 1H), 7.18 (t, 1H). MS (TSI$^+$): M/Z [MH$^+$] 332.1; C$_{21}$H$_{33}$NO$_2$+H requires 332.3.

Preparation 3: (±)-1-[trans-3,4-Dimethyl-4-(3-hydroxyphenyl)-1-piperidinyl]-3-tetrahydro-2H-pyran-2-yl-1-propanone To a solution of 3-(tetrahydro-2H-pyran-2-yl)propionic acid (Preparation 4, 0.243 g, 1.54 mmol), 1-(3-dimethylaminopropyl)-3-ethylcarbodiimide hydrochloride (0.42 g, 2.19 mmol) and 1-hydroxybenzotriazole (0.223 g, 1.65 mmol) in N,N-dimethylformamide (55 mL) at room temperature was added (±)-3-(trans-3,4-dimethylpiperidinyl)phenol (Reference 3, 0.338 g, 1.65 mmol). The mixture was stirred at room temperature for 48 hours and then water (50 mL) was added. The aqueous layer was extracted with diethyl ether (2×150 mL) and the combined organic layers were washed with brine (50 mL), dried (Na$_2$SO$_4$), filtered and concentrated in vacuo to give a clear residue. This was purified by column chromatography on silica gel, eluting with a gradient of ethyl acetate and hexane (66:44 to 75:25), to give the title compound (0.473 g, 90%) as a colourless oil.

NMR (CDCl$_3$, selected data from the free base (approximately a 1:1 mixture of isomers)): 0.59–0.68 (m, 3H), 1.38–1.41 (m, 3H), 2.87 (m, 0.5H), 3.15 (m, 0.5H), 3.50–3.70 (m, 1H), 3.90–4.02 (m, 1.5 H), 4.35 (m, 0.5H), 4.70 (m, 0.5H), 6.68 (d, 1H), 6.72–6.80 (m, 2H), 7.18 (t, 1H). MS (TSI$^+$): M/Z [MH$^+$] 346.3; C$_{21}$H$_{31}$NO$_3$+H requires 346.2.

Preparation 4: 3-(Tetrahydro-2H-pyran-2-yl)propionic acid

An aqueous solution of lithium hydroxide (4 mL of 2 M) was added to a solution of methyl 3-(tetrahydro-2H-pyran-2-yl)propionate (Preparation 5, 0.46 g, 2.67 mmol) in tetrahydrofuran (16 mL) and the reaction mixture was heated under reflux for 10 h. The cooled reaction mixture was acidified with aqueous 2N hydrochloric acid to pH 1, and then extracted with ethyl acetate (3×50 mL). The combined extracts were washed with brine (30 mL), dried (MgSO$_4$) and concentrated in vacuo to give the title compound as a colourless oil (460 mg, 67%).

NMR (CDCl$_3$): 1.10–1.20 (m, 1H), 1.40–1.60 (m, 4H), 1.70–1.90 (m, 3H), 2.50 (dt, 2H), 3.25–3.25 (m, 1H), 3.40 (m, 1H) and 3.95 (d, 1H). MS (TSI$^+$): M/Z [MH$^+$] 159.2; C$_8$H$_{14}$O$_3$+H requires 159.1.

Preparation 5: Methyl 3-(tetrahydro-2H-pyran-2-yl)propionate

A mixture of methyl (E)- and (Z)-3-(tetrahydro-2H-pyran-2-yl)-2-propenoate (Reference 4, 0.537 g, 3.15 mmol) was dissolved in methanol (10 mL) containing 10% palladium on charcoal (0.050 g) and was subjected to hydrogenation at 415 kPa and room temperature overnight. The reaction mixture was filtered through Celite®, the residue washed with methanol and the combined filtrates concentrated in vacua. The crude product was purified by column chromatography on silica gel (30 g), eluting with diethyl ether:hexane (1:4), to give the title compound as a colourless oil (470 mg, 87%).

NMR (CDCl$_3$): 1.21 (q, 1H), 1.50–1.60 (m, 4H), 1.70–1.80 (m, 3H), 2.40 (m, 2H), 3.15–3.25 (m, 1H), 3.35 (t, 1H), 3.62 (s, 3H) and 3.90 (d, 1H).

Preparation 6: (±)-3-{1-[2-(Cyclohexyloxy)ethyl]-trans-3,4-dimethyl-4-piperidinyl}phenol A solution of (±)-3-(trans-3,4-dimethylpiperidinyl)phenol (Reference 3, 2.43 g, 12 mmol) in 1,2-dimethoxyethane (100 mL) was stirred under nitrogen. Sodium hydrogencarbonate (1.41 g, 16.7 mmol) was added followed by 2-(cyclohexyloxy)ethyl 4-bromobenzenesulfonate (Preparation 7, 4.3 g, 12 mmol) and the reaction mixture was heated to 85° C. for 24 h. The reaction mixture was cooled to room temperature and then further cooled with stirring to 0° C. for 15 min. The solid was filtered off and the filtrate was concentrated in vacuo. The crude residue was purified by flash chromatography on silica gel, eluting with hexane:ethyl acetate (2:1), to give the title compound (2.5 g, 64%).

NMR (CDCl$_3$, selected data for the free base): 0.8 (d, 3H), 1.3 (s, 3H), 2.8–2.9 (m, 1H), 3.2–3.3 (m, 1H), 3.5–3.65 (m, 2H), 6.6 (d, 1H), 6.75 (s, 1H), 6.85 (d, 1H), 7.15 (t, 1H). MS (TSI$^+$): M/Z [MH$^+$] 332.2; C$_{21}$H$_{33}$NO$_2$+H requires 332.3.

Preparation 7: 2-(Cyclohexyloxy)ethyl 4-bromobenzenesulfonate

A solution of 2-cyclohexyloxyethanol (4.56 g, 32 mmol) and triethylamine (22 mL, 160 mmol) in dichloromethane (225 mL) was stirred under nitrogen. A saturated solution of 4-bromobenzenesulfonyl chloride (9.0 g, 35 mmol) in dichloromethane was added dropwise at 0° C., and the reaction mixture was stirred overnight under nitrogen. The reaction mixture was then washed with 1N aqueous hydrochloric acid (2×200 mL) and the organic layer separated. The organic layer was washed sequentially with water (200 mL) and brine (200 mL), dried (MgSO$_4$) and then concentrated in vacuo to give a white solid. The crude solid was dissolved in the minimum amount of dichloromethane and purified by passing through a plug of silica, which was eluted with ethyl acetate:hexane (50:50), ethyl acetate (100%) and finally methanol:ethyl acetate (10:90). The title compound was obtained as a yellow oil (4.3 g, 41%).

NMR (CDCl$_3$, selected data): 3.1–3.35 (m, 2H), 4.1–4.3 (t, 2H), 7.7 (d, 2H), 7.8 (d, 2H). MS (TSI$^+$): M/Z [MNH$_4^+$] 379.9; C$_{14}$H$_{19}$BrO$_4$S+NH$_4$ requires 380.1.

REFERENCES

1 J. U. Patel, R. J. Prankerd and K. B. Sloan, *J. Pharmaceutical Sciences*, 1994, 83, 10, 1477.
2. I. G. C. Coults, N. R. Southcott, *J. Chem. Soc., Perkin 1*, 1990, 767.
3. a) J A Werner et al, *J. Org. Chem.*, 1996, 61, 587; b) C. H. Mitch, D. M. Zimmerman, J. D. Snoddy, J. K. Reel, and B. E. Cantrell, *J. Org. Chem.*, 1991, 56, 1660.
4. H. Priepke and R. Brückner, *Chem. Ber.*, 1990, 123, 153

The invention claimed is:
1. A compound of formula I,

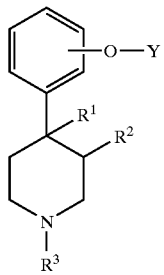

I wherein the group OY is attached to the benzene ring in the position meta-relative to the piperidine group;
$R^1$ is $C_{1-4}$ alkyl;
$R^2$ is H or $C_{1-4}$ alkyl;
$R^3$ represents
(i) $C_{1-10}$ alkyl,
(ii) $C_{3-10}$ alkenyl, or
(iii) $C_{3-10}$ alkynyl,
wherein said alkyl, alkenyl or alkynyl groups are optionally substituted and/or terminated by one or more substituents selected from OR$^{4c}$, S(O)$_n$R$^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, N(R$^{5a}$)S(O)$_2$R$^6$, Het$^1$, aryl, adamantyl (which latter two groups are optionally substituted by one or more substituents selected from OH, nitro, amino, halo, CN, CH$_2$CN, CONH$_2$, $C_{1-4}$ alkyl, $C_{1-4}$ alkoxy and $C_{1-5}$ alkanoyl (which latter three groups are optionally substituted by one or more halo atoms)), or -W-A$^1$-N(R$^{5b}$)(R$^{5c}$);
n is 0, 1 or 2;
W represents a single bond, C(O) or S(O)$_p$;
A$^1$ represents a single bond or $C_{1-10}$ alkylene; provided that when both W and A$^1$ represent single bonds, then the group —N(R$^{5b}$)(R$^{5c}$) is not directly attached to an unsaturated carbon atom;
p is 0, 1 or 2;
$R^{4c}$ and $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, CH$_2$CN, CONH$_2$, $C_{1-4}$ alkyl, $C_{1-4}$ alkoxy and $C_{1-5}$ alkanoyl (which latter three groups are optionally substituted by one or more halo atoms)) or Het$^2$; provided that $R^{4d}$ does not represent H when n represents 1 or 2;
$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, CH$_2$CN, CONH$_2$, $C_{1-4}$ alkyl, $C_{1-4}$ alkoxy and $C_{1-5}$ alkanoyl (which latter three groups are optionally substituted by one or more halo atoms)), or Het$^3$,
or $R^{5b}$ and $R^{5c}$ together represent unbranched $C_{2-6}$ alkylene which alkylene group is optionally interrupted by O, S and/or an N(R$^7$) group and is optionally substituted by one or more $C_{1-4}$ alkyl groups;
$R^6$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;
$R^7$ represents H, $C_{1-6}$ alkyl, $C_{3-8}$ cycloalkyl, A$^2$-(C$_{3-8}$ cycloalkyl) or A$^2$-aryl; A$^2$ represents $C_{1-6}$ alkylene;
Het$^1$, Het$^2$ and Het$^3$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);
Y represents $R^{11}$;
$R^8$ and $R^9$ independently represents H, $C_{1-10}$ alkyl, $C_{3-10}$ alkenyl (which latter two groups are optionally substituted by one or more aryl or $C_{4-7}$ cycloalyl groups (which two groups are optionally substituted by one or more substituents selected from halo, $C_{1-4}$ alkyl, $C_{1-4}$ alkoxy, $C_{1-4}$ haloalkyl or $C_{1-4}$ haloalkoxy)), aryl, $C_{4-7}$ cycloalkyl (optionally substituted by one or more substituents selected from halo, $C_{1-4}$ alkyl and $C_{1-4}$ alkoxy (which latter two groups are optionally substituted by one or more halo atoms)),
or $R^8$ and $R^9$, together with the N-atom to which both are attached, represent Het$^4$; Het$^4$ represents a 5- to 8-membered heterocyclic ring comprising at least one nitrogen atom and optionally one or more additional heteroatoms selected from oxygen and sulfur, which heterocyclic ring is optionally substituted by one or more $C_{1-4}$ alkyl groups;
$R^{11}$ represents
(i) $C_{4-7}$ cycloalkyl (optionally substituted by one or more $C_{1-4}$ alkyl groups),
(ii) $C_{6-10}$ alkyl,
(iii) $C_{3-10}$ alkenyl,
which alkyl or alkenyl group is optionally substituted by one or more substituents selected from C(O)NH$_2$, Het$^6$, $C_{4-7}$ cycloalkyl (optionally substituted by one or more $C_{1-4}$ alkyl groups), aryl, aryloxy or
aryl($C_{1-4}$)alkoxy (which latter three groups are optionally substituted by one or more substituents selected from OH, halo, $C_{1-4}$ alkanoyl, $C_{1-4}$ alkanoyloxy, N(R$^8$)(R$^9$), C(O)N(R$^8$)(R$^9$), $C_{1-4}$ alkyl and $C_{1-4}$ alkoxy (which latter two groups are optionally substituted by one or more halo atoms)), or (iv) $C_{1-5}$ alkyl substituted by one or more substituents selected from $C(O)NH_2$, $Het^8$, $C_{4-7}$ cycloalkyl (optionally substituted by one or more $C_{1-4}$ alkyl groups), aryl, aryloxy or aryl($C_{1-4}$)alkoxy (which latter three groups are optionally substituted by one or more substituents selected from OH, halo, $C_{1-4}$ alkanoyl, $C_{1-4}$ alkanoyloxy, $N(R^8)(R^9)$, $C(O)N(R^8)(R^9)$, $C_{1-4}$ alkyl and $C_{1-4}$ alkoxy (which latter two groups are optionally substituted by one or more halo atoms)); p1 $Het^6$ and $Het^8$ each independently represent 4- to 6-membered heterocyclic rings, which rings contain at least one heteroatom selected from oxygen, sulfur, and/or nitrogen, which rings are optionally fused to a benzene ring, and which rings are optionally substituted in the heterocyclic and/or fused benzene ring part by one or more substituents selected from OH, =O, nitro, amino, halo, CN, aryl, $C_{1-4}$ alkyl, $C_{1-4}$ alkoxy, $C_{3-6}$ cycloalkyl and $C_{1-5}$ alkanoyl (which latter four groups are optionally substituted by one or more halo atoms);

or a pharmaceutically, or a veterinarily, acceptable derivative thereof.

2. A compound as claimed in claim 1 wherein $R^1$ represents $C_{1-2}$ alkyl.

3. A compound as claimed in claim 1 wherein $R^2$ represents H or $C_{1-2}$ alkyl.

4. A compound as claimed in claim 1 wherein $R^3$ represents $C_{1-6}$ alkyl, $C_{3-6}$ alkenyl or $C_{3-6}$ alkynyl wherein said alkyl, alkenyl or alkynyl groups are optionally substituted and/or terminated by one or more substituents selected from $OR^{4c}$, CN, halo, $Het^1$ or aryl (which latter group is optionally substituted by one or more substituents selected from OH, $C_{1-2}$ alkyl, $C_{1-2}$ alkoxy or halo).

5. A compound as claimed in claim 1 wherein $R^{4c}$ represents H, $C_{1-6}$ alkyl, $C_{4-6}$ cycloalkyl, aryl or $Het^2$.

6. A compound as claimed in claim 1 wherein $Het^1$ and $Het^2$ independently represent 5- to 7-membered heterocyclic groups, which groups contain at least one heteroatom selected from oxygen, sulfur and/or nitrogen, and which groups are optionally substituted by one or more $C_{1-2}$ alkyl groups (which alkyl groups are optionally substituted by one or more halo atoms).

7. A compound as claimed in claim 1 wherein $R^8$ and $R^9$ independently represent H or $C_{1-4}$ alkyl; $R^{10}$ represents $C_{1-6}$ alkyl (substituted by one or more phenyl groups) or aryl (optionally substituted by one or more substituents selected from OH, halo, $C_{1-3}$ alkanoyloxy, $NH_2$, $C(O)NH_2$ and $C_{1-3}$ alkyl (which latter group is optionally substituted by one or more halo atoms)); and/or $R^{11}$ represents $C_{1-5}$ alkyl (substituted by one or more substituents selected from $C(O)NH_2$, $Het^8$, aryl and aryloxy), $C_{6-10}$ alkyl or $C_{3-10}$ alkenyl, which latter two groups are optionally substituted by one or more substituents selected from $Het^6$ and aryl.

8. A compound as claimed in claim 1 wherein $Het^6$ and $Het^8$ independently represent 5- to 6-membered heterocyclic rings, which rings contain at least one heteroatom selected from oxygen, sulfur and/or nitrogen, which rings are optionally fused to a benzene ring, and which rings are optionally substituted in the heterocyclic and/or fused benzene ring part by one or more substituents selected from OH, =O and $C_{1-4}$ alkyl).

9. A compound as claimed in claim 1 wherein $Het^6$ and $Het^8$ are in S-oxidized form.

10. A pharmaceutical composition comprising a pharmaceutically effective amount of a compound as defined in claim 1, in admixture with a pharmaceutically, or a veterinarily, acceptable adjuvant, diluent or carrier.

11. A pharmaceutical composition as claimed in claim 10, which is a veterinary formulation.

12. A method of treating pruritus, which comprises administering a therapeutically effective amount of a compound as defined in claim 1, to a patient in need of such treatment.

13. A process for the preparation of a compound as defined in claim 1, which comprises:
a) for compounds of formula I wherein $R^3$ represents $C_1$ alkyl optionally substituted by $C_{3-8}$ cycloalkyl, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $R^3$ represents $C_{2-10}$ alkyl, $C_{3-10}$ alkenyl or $C_{3-10}$ alkynyl (which three groups are all optionally substituted by one or more of the relevant substituents identified in claim 1 in respect of $R^3$), which alkyl, alkenyl or alkynyl groups are attached to the piperidine nitrogen atom via a $CH_2$ group, wherein $Het^1$ is as defined in claim 1, reduction of a corresponding compound of formula II,

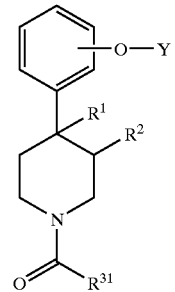

II wherein $R^{31}$ represents H, $C_{3-8}$ cycloalkyl, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $-W-A^1-N(R^{5b})(R^{5c})$, and $R^1$, $R^2$, $R^{4c}$, $R^{4d}$, $R^{5a}$ to $R^{5c}$, $R^6$, $Het^1$, n, Y, W and $A^1$ are as defined in claim 1;

b) reaction of a corresponding compound of formula III,

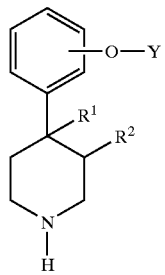

III wherein $R^1$, $R^2$ and Y are as defined in claim 1, with a compound of formula V, $R^3\text{-}L^1$    V wherein $L^1$ represents a leaving group and $R^3$ is as defined in claim 1;

c) for compounds of formula I wherein $R^3$ represents $C_1$ alkyl, which, in place of being optionally substituted by the substituents as defined in claim 1, is instead optionally substituted by $R^{31}$, wherein $R^{31}$ is as defined above, reaction of a corresponding compound of formula III, as defined above, with a compound of formula VI, $R^{31}\text{CHO}$    VI wherein $R^{31}$ is as defined above, in the presence of a reducing agent;

d) for compounds of formula I wherein $R^3$ is a $C_{1\text{-}10}$ alkyl, $C_{4\text{-}10}$ alkenyl or $C_{4\text{-}10}$ alkynyl group that is fully saturated from 1- to 3-C (relative to the piperidine N-atom), and which $R^3$ group is substituted at 2-C (relative to the piperidine N-atom) by $S(O)R^{4d}$, $S(O_2R^{4d}$, alkanoyl, cycloalkanoyl, alkoxy carbonyl, CN, —C(O)-$A^1$-N($R^{5b}$)($R^{5c}$), —S(O)-$A^1$-N($R^{5b}$)($R^{5c}$), or —S(O)$_2$-$A^1$-N($R^{5b}$)($R^{5c}$), wherein $R^{4d}$, $R^{5b}$, $R^{5c}$ and $A^1$ are as defined in claim 1, reaction of a corresponding compound of formula III, as defined above, with a compound of formula VII, $R^{3a}\text{-}Z$    VII wherein $R^{3a}$ represents $R^3$ as defined in claim 1, and that the $R^{3a}$ chain contains an additional carbon-carbon double bond α,β to the Z-substituent, and Z represents $S(O)R^{4d}$, $S(O)_2R^{4d}$, alkanoyl, cycloalkanoyl, alkoxy carbonyl, CN, —C(O)-$A^1$-N($R^{5b}$)($R^{5c}$), —S(O)-$A^1$-N($R^{5b}$)($R^{5c}$), or —S(O)$_2$-$A^1$-N($R^{5b}$)($R^{5c}$), wherein $R^{4d}$, $R^{5b}$, $R^{5c}$ and $A^1$ are as defined in claim 1;

e) for compounds of formula I in which Y represents $R^{11}$, wherein $R^{11}$ is as defined in claim 1, reaction of a corresponding compound of formula VIII,

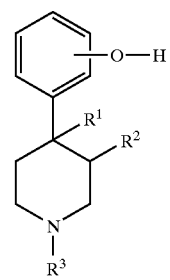

VIII wherein $R^1$, $R^2$ and $R^3$ are as defined in claim 1, with a compound of formula XVI, $R^{11}\text{-}L^2$    XVI wherein $L^2$ represents a leaving group and $R^{11}$ is as defined in claim 1.

* * * * *